US011172818B1

(12) United States Patent
Theimer et al.

(10) Patent No.: US 11,172,818 B1
(45) Date of Patent: Nov. 16, 2021

(54) STREAMING ANALYTICS OF HUMAN BODY MOVEMENT DATA

(71) Applicant: Amazon Technologies, Inc., Seattle, WA (US)

(72) Inventors: Marvin Theimer, Bellevue, WA (US); Richard Shawn Bice, Sammamish, WA (US)

(73) Assignee: Amazon Technologies, Inc., Seattle, WA (US)

( * ) Notice: Subject to any disclaimer, the term of this patent is extended or adjusted under 35 U.S.C. 154(b) by 433 days.

(21) Appl. No.: 16/055,345

(22) Filed: Aug. 6, 2018

(51) Int. Cl.
*G06F 3/01* (2006.01)
*A61B 5/00* (2006.01)
*G06T 7/20* (2017.01)
*G06K 9/00* (2006.01)
*G06N 20/00* (2019.01)

(52) U.S. Cl.
CPC ............ *A61B 5/0002* (2013.01); *G06F 3/011* (2013.01); *G06K 9/00342* (2013.01); *G06N 20/00* (2019.01); *G06T 7/20* (2013.01)

(58) Field of Classification Search
CPC .......... G06F 19/18; G06F 19/24; G06F 19/20; G06F 19/16; G06G 19/22
USPC ........................................................... 702/19
See application file for complete search history.

(56) References Cited

U.S. PATENT DOCUMENTS

| 2012/0223833 | A1* | 9/2012 | Thomas | G16H 50/30 340/539.12 |
| 2016/0287177 | A1* | 10/2016 | Huppert | A61B 5/0006 |
| 2016/0338644 | A1* | 11/2016 | Connor | A61B 5/1071 |
| 2017/0259115 | A1* | 9/2017 | Hall | G06F 19/00 |

\* cited by examiner

*Primary Examiner* — Gordon G Liu
(74) *Attorney, Agent, or Firm* — Lee & Hayes, P.C.

(57) ABSTRACT

Large amounts of human body movement data may be collected, possibly via streaming data, from one or more sensors worn by a user. The data may be analyzed along with other classification data to generate feedback for the user or for other interested people (e.g., a trainer, a coach, a team member, health professional, etc.). The analysis may utilize one or more machine learning (ML) algorithms that use training data to create one or more ML models. When a user is evaluated after receiving feedback, accuracy of the feedback may be evaluated and fed back to the ML model to continue training the ML model(s).

20 Claims, 14 Drawing Sheets

STREAMING ANALYTICS OF HUMAN BODY MOVEMENT DATA

BACKGROUND

When a person is active, whether it be for recreation or for work, it can be helpful to monitor one's body to make informed decisions on intensity levels of the activity and on the duration of the activity. For example, when a person is cycling over a long distance, the person may desire to track his or her heart rate, water consumption, food consumption and distance traveled. Some people use smart watches, such as those designed by Garmin® and Fitbit® to provide heart rate, calories, and/or distance traveled. However, these devices have limitations on the type of information they can collect, how they analyze the information, and how they can report this information back to a user or other users.

Processing a stream of continuous data can be difficult, especially by a low power device that lacks reliable connectivity to more powerful processing devices. For example, a watch typically has limited processing capabilities and is unable to handle processing large amounts of streaming data. Instead, watches and similar devices typically measure few metrics and report basic information about the metrics. Streaming data may include data from many different sensors and from a number of different devices. To process streaming data, it is often desirable to use an elastic resource that can be expanded or scaled based on an amount of the streaming data.

BRIEF DESCRIPTION OF THE DRAWINGS

The detailed description is described with reference to the accompanying figures. In the figures, the left-most digit(s) of a reference number identifies the figure in which the reference number first appears. The same reference numbers in different figures indicate similar or identical items.

DETAILED DESCRIPTION

Figure 1:
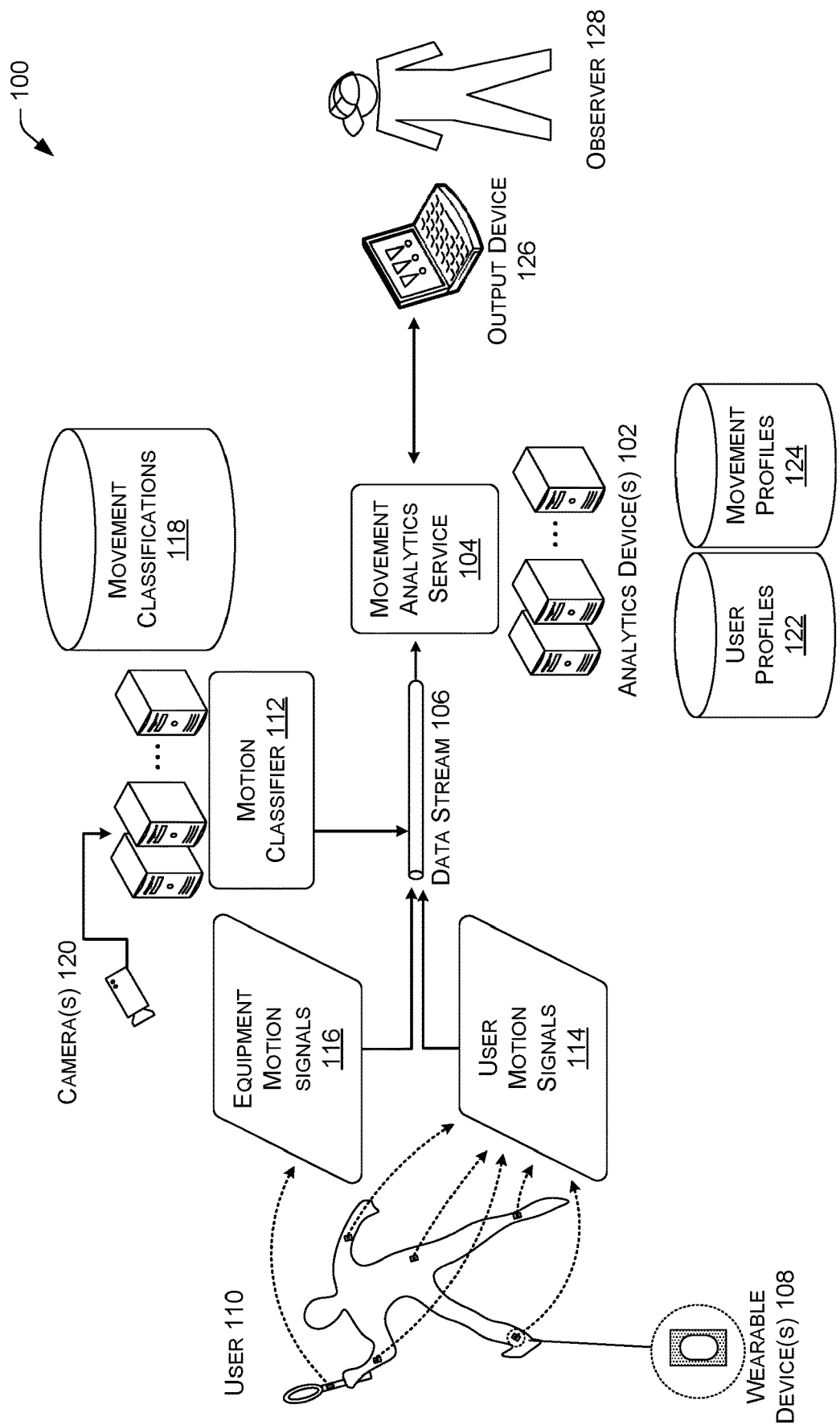
FIG. 1 is a block diagram of an illustrative environment that performs streaming analytics of human body movement data.

This disclosure is directed to collecting large amounts of human body movement data, possibly via streaming data, from one or more sensors worn by a user, analyzing the data along with other classification data, and outputting feedback for the user or other interested people (e.g., a trainer, a coach, a team member, health professional, etc.). The analysis may utilize one or more machine learning (ML) algorithms that use training data to create one or more ML models. When a user is evaluated after receiving feedback, accuracy of the feedback may be evaluated and fed back to the ML model to continue training the ML model(s).

Wearable devices may be any devices that are affixed or worn by a user during the movement. In some embodiments, the wearable devices may include a patch (e.g., adhesive patch), a band, clothing, equipment (e.g., a racquet, a ball, a helmet, pads, etc.), or other wearable objects (e.g., a wristband, a headband, gloves, shoes, glasses, etc.). Furthermore, the wearable devices may include sensors that are integrated into any type of material associated with the user, such as clothing of the user. For instance, the sensors may be affixed to the material (e.g., using an adhesive), or stitched/woven into the material (e.g., inserted within or on a shoulder pad of an article of clothing) Clothing intended for a particular type of activity (e.g., sports, dance, yoga, etc.) may include any number of sensors in a variety of locations on the clothing that collect and transmit any type of movement and/or other information about the activity of the user. The wearable device(s) may include a radio (e.g., a transmitter or transceiver), one or more accelerometers, and/or other sensors to measure movement and/or information about a user, possibly including information such as perspiration, temperature, or other information.

The motion of the user may be classified to create a motion description, which may then be associated with motion signals and/or other signal data output by the wearable device(s). For example, classification information of user movement may be received, such as a physical therapy exercise, a dance routine, football play (i.e., plan of action), military drill, a gymnastics event, or other movement or series of movements that are repeatable and have similarities that enable extracting patterns from multiple captures of data corresponding to repeat performances of the movement. The movement associated with a motion description may be a short discrete motion or may be a longer series of movements, such as those associated with a certain position player executing a football play in American football, which uses a plan of attack strategy referred to as a "play".

As a first example of use of the streaming analytics techniques described herein, the systems and/or techniques may be used to analyze users to determine when an injury is likely if current activity or more rigorous activity continues for a duration of time. For example, a football player may wear one or more wearable devices that provide information about movement of the user and/or other user information. The information may be classified based on a type of play that the user performs (e.g., long pass route, blocking route, ball carrying run play, etc.). The analysis system may compare current movement data and other user data for a given play to prior historical movement data and/or other user data, possibly using thresholds or other quantified metrics that describe the movement. The thresholds and/or other metrics may be correlated to injuries based on training of a model, which may receive feedback from time to time from new information that classifies recent movement data (e.g., such as movement data associated with an actual injury). Injuries may include pulling a muscle, cramping, torn ligaments/tendons/sinews/muscles, exhaustion, dehydration, heat stroke, etc.), Thus, the analysis of current data from a movement (e.g., user running a pass route) may be used to determine if the user is at risk for an injury and should take precautionary actions, such as taking a rest break, rehydrating, slowing down, or taking other actions.

As another example of the streaming analytics techniques described herein, the systems and/or techniques may be used to detect occurrence of an actual injury. For example, a military cadet may wear one or more wearable devices that provide movement and/or other user information about his/her body performance to an analytics device. The analytics device may receive movement description data, which enables classifying the movement data and/or other user information and comparing that movement data and/or other user information to thresholds and/or historical data that may correlate to an occurrence of an actual injury. As an example, the cadet may move in a normal manner, become injured, and then move in an abnormal, unusual, or different manner, such as by limping, slowing down, or making other changes to the normal movement previous exhibited by the cadet. The techniques may determine the change in movement and/or other information, and may determine an injury associated with the change based at least in part on a learning model that uses historical information to classify new information. The techniques may determine a specific type of injury, such as an injury of a sprain of a particular joint of the user, for example, among many other types of injuries.

As yet another example of the streaming analytics techniques described herein, the systems and/or techniques may be used to determine when to take a rest or other restorative action to prolong the activity and/or for other reasons. For example, the movement data may track movement of a user playing a competitive game of tennis. The movement data, when classified and analyzed, may indicate a level of fatigue of the user based on a comparison to thresholds, baseline data, and/or other historical data. The analytics device(s) may determine a recommended time for a rest to reduce fatigue of the user and enable the user to return to the activity at a higher performance level than prior to the rest. Movement data after the rest may be used to train the model to identify an optimized time for the rest and duration of the rest, within certain constraints, such as constraints associated with rules of play for a sport, employment guidelines, and so forth. Thus, the analytics device, which may employ one or more ML algorithms and/or one or more ML models, may continue to update and "learn" based on received movement data and analysis of that data, possibly with other inputs, such as user inputs that classify the data.

As still another example of the streaming analytics techniques described herein, the systems and/or techniques may be used to evaluate movement as conforming on non-conforming to an expected type of movement. For example, a user may be performing a physical therapy routine, such as a particular stretching exercise. The movement data of the user performing the activity may be compared to movement data associated with correct performance of the activity by the user or by another user or group of users. The analytics device may determine, based on current movement data and classification thereof, whether the user is performing the activity correctly, incorrectly, and/or some degree therebetween. For example, the analytics device may generate a score that indicates a level or degree of compliance with correct performance of the activity, possibly based on factors such as time (e.g., too fast, too slow, etc.), movement range (e.g., too far, not far enough, etc.), angle of movement (wrong angle, etc.) and/or other movement information and/or user information.

An output may be an output of metrics and/or a recommendation, such as to hydrate, take a rest, reduce level of output or activity, discontinue activity, etc. The output may be provided from time to time, such as when thresholds are reached or exceeded. The output may be provided to a special device, such as a device associated with a trainer, a coach, a teammate, a health professional or another person.

The techniques and systems described herein may be implemented in a number of ways. Example implementations are provided below with reference to the following figures.

FIG. 1 is a block diagram of an illustrative environment 100 that performs streaming analytics of human body movement data. The environment 100 may include one or more analytics device 102 that performs the analytics of movement data as discussed herein. The analytics device 102 may provide a movement analytics service 104 that analyzes user body movement data streamed, via a data stream 106, from one or more wearable devices 108, possibly via an intermediate device that is local to the wearable device(s). The data stream may be initiated by the analytics device 102 and/or one or more of the wearable devices 108 to create a secure connection and flow of data between the wearable devices 108 and the analytics device 102. An example of a data streaming service is Amazon Kinesis® by Amazon.com Inc (dba "Amazon"), of Seattle, Wash. The data stream may receive movement data and/or other user data from the wearable devices 108 worn by a user 110 or otherwise manipulated by the user 110 (e.g., equipment, etc.), possibly along with metadata, such as time information. For example, the wearable devices may output signals to the data stream 106 and may include time stamps and/or other information, possibly including an indication of a new action or movement or a classification of a movement or action. However, classification of movements may also be provided by the motion classifier 112, described below. The wearable devices may include accelerometer(s) and other motion tracking devices (e.g., a global position system (GPS) device, a trackable identifier, load cells, and/or other devices that track forces, movement, impacts, and the like). The wearable devices may send the signals as movement data and/or other user data to the data stream 106 for delivery to the movement analytics service 104 for further processing. The wearable devices 108 may include devices worn by user, which produce user motion signals 114 and/or equipment manipulated by users that produce equipment motion signals 116, such as sporting equipment (e.g., a racquet, a ball, a disc, a bike, etc.), work equipment, and so forth. As an example, the user motion signals 116 and/or the equipment motion signals 116 may include signals from an accelerometer, signals from a temperature sensor (e.g., a thermocouple, etc.), signal from a moisture sensor, and/or signals from other measurement devices.

The motion classifier 112 may classify movement, motion, and/or an action of the user using movement classifications 118. In some embodiments, the motion classifier 112 may receive input from a user or device that classifies the motion. For example, a coach or play caller (e.g., an offensive coordinate or football, etc.) may input a play. In some embodiments, the play may be determined by crowdsourcing (e.g., from fans, from broadcasters, etc.). New classifications may be added to the movement classifications 118. In various embodiments, one or more cameras 120 may capture imagery of the movement, which may be processed by image analysis algorithms that classify for the motion classifier 112. By classifying the movement, the user motion signals 114 and/or the equipment motion signals 116 may be associated with the classification for use in analysis of the data from the data stream 106. The classification may be of a discrete event, movement, or event, which may have a duration of less than a second, of seconds, or of minutes, for example. The classification data may be output to the data stream 106 for conveyance to the movement analytics service 104. The data stream 106 may also convey other relevant data to the movement analytics service 104.

The analytics device 102 may receive data via the data stream 106, including at least the user motion signals 114 and the motion classification via the motion classifier 112. In some embodiments, the motion classifier 112 may be part of the movement analytics service 104. The movement analytics service 104 may access user profiles 122 and/or movement profiles 124 to create, store, and/or access data. The user profile 122 may include data about the user. Each user may include different information, such as different movement data or other user data. The movement profiles may include ML model(s) and/or other data to determine movements, movement thresholds, predictions, alerts, and/or other information by leveraging historical information about movements and/or other data received via the data stream at a prior time and/or at a present time (i.e., current data).

In various embodiments, the movement analytics service 104 may receive the movement signals and the motion description data, generate a historical profile for the user of the wearable patch based at least in part on the movement signals and the motion description data, create at least one of a fatigue metric threshold or an injury metric threshold based at least in part on the historical profile, and analyze movement signals and motion description associated with the movement signals to determine user information including at least one of a fatigue metric associated with the user or an injury prediction metric associated with the user.

In addition to injury or fatigue, the historical profile, the movement signals, and/or the motion description data may correspond to a proper motion or form that is expected in association with an activity. Such activities may include physical therapy, physical training, exercise activity (e.g., yoga, dance, etc.), etc. in which the user 110 is participating. The movement signals and/or the motion description data, possibly in association with historical data relating to the user 110 and other users 110, may indicate that the user 110 is not using the proper or expected form for a particular activity. In some instances, using improper form may result in injury. Upon determining that the user 110 is using improper form, such information may be output to an output device 126 for output to an observer 128.

In some embodiments, the movement analytics service 104 may access training data associated with a user. For example, the movement analytics service 104 may receive movement and other data from devices that measure movement of the user. The data may be classified by a type of movement, characteristics of the movement (e.g., practice, game, intense, casual, etc.), and may be associated with outcomes (e.g., right before an injury, after an injury, etc.).

The movement analytics service 104 may then generate thresholds and/or other indications using the historical trained data. The thresholds may trigger output of alerts, recommendations, and/or other outputs by the movement analytics service 104. The analytics device 102 may transmit outputs from time to time to the output device 126 for receipt by the observer 128, such as a trainer, a coach, a teammate, a health professional, and/or another person. In some embodiments, the observer 128 may inspect the user 110 and provide additional information back to the analytics device, which may be used as training data and may be used to update one or more of the ML models used by and/or maintained by the analytics device 102.

Figure 2A:
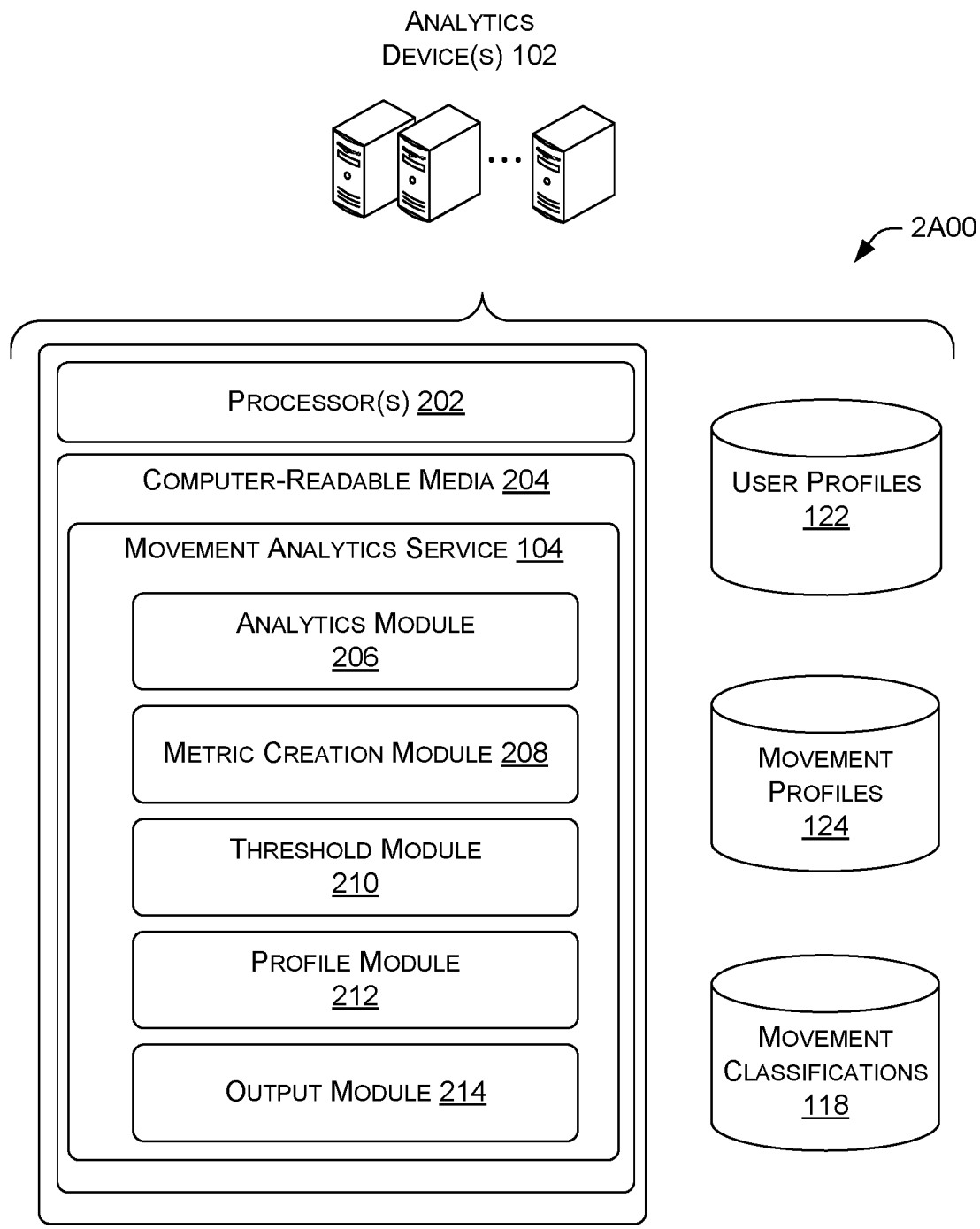
FIG. 2A is a block diagram of an illustrative computing architecture of the analytics device(s) shown in FIG. 1.

FIG. 2A is a block diagram of an illustrative computing architecture 200 of the analytics device(s) shown in FIG. 1. The computing architecture 200 may be implemented in a distributed or non-distributed computing environment.

The computing architecture 200 may include one or more processors 202 and one or more computer readable media 204 that stores various modules, applications, programs, or other data. The computer-readable media 204 may include instructions that, when executed by the one or more processors 202, cause the processors to perform the operations described herein for the movement analytics service 104.

Embodiments may be provided as a computer program product including a non-transitory machine-readable storage medium having stored thereon instructions (in compressed or uncompressed form) that may be used to program a computer (or other electronic device) to perform processes or methods described herein. The machine-readable storage medium may include, but is not limited to, hard drives, floppy diskettes, optical disks, CD-ROMs, DVDs, read-only memories (ROMs), random access memories (RAMs), EPROMs, EEPROMs, flash memory, magnetic or optical cards, solid-state memory devices, or other types of media/machine-readable medium suitable for storing electronic instructions. Further, embodiments may also be provided as a computer program product including a transitory machine-readable signal (in compressed or uncompressed form). Examples of machine-readable signals, whether modulated using a carrier or not, include, but are not limited to, signals that a computer system or machine hosting or running a computer program can be configured to access, including signals downloaded through the Internet or other networks.

In some embodiments, the computer-readable media 204 may store the movement analytics service 104 ("service 104"). The service 104 may include an analytics module 206, a metric creation module 208, a threshold module 210, a profile module 212, and an output module 214, which are described in turn. The modules may be stored together or in a distributed arrangement. The computing architecture may include or have access to the user profiles 122, the movement profiles 124, and the movement classifications 118. The movement classifications 118 may include movement definitions and/or information to determine movement definitions from other sources, such as imagery analysis and/or from crowdsourcing (e.g., crawling fan commentary, analyzing broadcast audio, etc.).

The analytics module 206 may receive the movement signals from the wearable device(s), possibly including signals from equipment. The analytics module 206 may also receive corresponding movement descriptions associated with the signals, which provide classifications of the movements. The analytics module may create, update, and maintain machine learning models that compile training data and create predictive models to predict fatigue levels, possible injuries, actual injuries, improper form, movement profiles (e.g., correct movement according to an anticipated movement, such as a physical therapy activity, etc.), among other possible models.

The machine learning model(s) may represent a single model or an ensemble of base-level machine learning models, and may be implemented as any type of machine learning model. For example, suitable machine learning models for use with the techniques and systems described herein include, without limitation, tree-based models, k-Nearest Neighbors (kNN), support vector machines (SVMs), kernel methods, neural networks, random forests, splines (e.g., multivariate adaptive regression splines), hidden Markov model (HMMs), Kalman filters (or enhanced Kalman filters), Bayesian networks (or Bayesian belief networks), expectation maximization, genetic algorithms, linear regression algorithms, nonlinear regression algorithms, logistic regression-based classification models, or an ensemble thereof. An "ensemble" can comprise a collection of models whose outputs (classifications) are combined, such as by using weighted averaging or voting. The individual machine learning models of an ensemble can differ in their expertise, and the ensemble can operate as a committee of individual machine learning models that is collectively "smarter" than any individual machine learning model of the ensemble.

As mentioned, the output of the machine learning model(s), which typically processes unknown data as a subject for classification, may include, inter alia, a classification of the unknown data as a type of data among different types of data corresponding to different levels of relevance. The output may include additional information as well, such as an object identifier of the data object that includes the classified data, an object name of the data object, and the like. As an example, data may be classified as "low fatigue" or "high fatigue" when the model predicts a level of fatigue based at least in part on the received signals The training data may be updated in response to input from a recipient of the output of the model. For example, if the output of the model indicates an injury, but no injury is actually present, this information may be used to further train the model. For example, an athletic trainer or other person may evaluate the user and provide feedback to the analytics module 206, which may be used to further train one or more of the models.

In some embodiments, the analytics module 206 may create different models for different types of movement descriptions or may use the movement descriptions to classify data. Some data may not be used based on the movement description, for example, since that type of movement data may correlate well with a predictable outcome (e.g., the data may be chaotic and not accurately predictive of useful outputs). The movement profiles 124 may include ML models, algorithms, and raw data.

In addition to, or instead of, using machine learning, the analytics module 206 may use other types of analysis/analytic functions, such as probabilistic models or functions, predictive models, and so on. In some instances, the analytics module 206 may use these analysis/analytics functions to determine and assign probabilities to motion exhibited by the user 110. The probabilities may indicate a probability or a probability distribution that a particular movement may result in, or may result from, injury, fatigue, improper form, and so on.

The metric creation module 208 may create metrics based on the signals. The metrics may correspond to movements, such as acceleration metrics, range of motion metrics, and/or other movement data. The metrics may include other user or body information, such as temperature, perspiration metrics, a heart rate of the user 110, blood data associated with a blood sample obtained from the user 110, and so forth. The metric creation module 208 may provide inputs to the analytics module 206 to create the ML model(s). For example, the metric creation module 208 may convert the signals from the wearable devices into metrics for use by the analytics module 206.

In some embodiments, one or more sensors (e.g., thermometers, hygrometers, etc.) located in proximity to the user 110, or at least within an environment in which the user 110 is located, may obtain or detect data relating to the current ambient conditions of the environment. The data may include an ambient temperature or an ambient humidity associated with the environment. This ambient data may be considered in combination with data received from the wearable device(s) 108 (e.g., motion data, temperature data, perspiration data, heart rate data, etc.), and may be used to determine various metrics. Accordingly, data from external sources may also be utilized to determine or predict injury, fatigue, improper form, etc., of the user 110. Since ambient temperature and/or ambient humidity may affect a performance of the user 110 when engaging in various types of activities, the ambient data may be used to modify thresholds used in evaluating the metrics. For instance, if the ambient temperature is relatively warm or the ambient humidity is relatively high, the threshold may be decreased. As a result, the thresholds for a particular user 110 may vary over time, and thresholds for a first user 110 may vary with respect to different users 110.

The threshold module 210 may create thresholds for use in evaluating the metrics. Illustrative thresholds are shown in FIGS. 6A-6D and 7, which are described below. As an example, a threshold may indicate when a user's acceleration is below a normal range, which may indicate fatigue or an injury.

The profile module 212 may create information for the user profiles, which may customize user specific information such as weights for the ML models for specific users, thresholds for specific users, and/or other user information for specific users (e.g., temperature data, perspiration data, etc.). In some embodiments, the user profile information may be used by other modules, such as the analytics module 206.

The output module 214 may output or cause output of classifications, messages, alerts, and/or other data to an output device, which may be made available to the user or a person associated with the user, such as a trainer, a coach, a health profession, a teammate, and/or other people. The output module may provide a stream of outputs and/or may provide specific outputs from time to time, such as alerts about fatigue levels or possible injury.

Figure 2B:
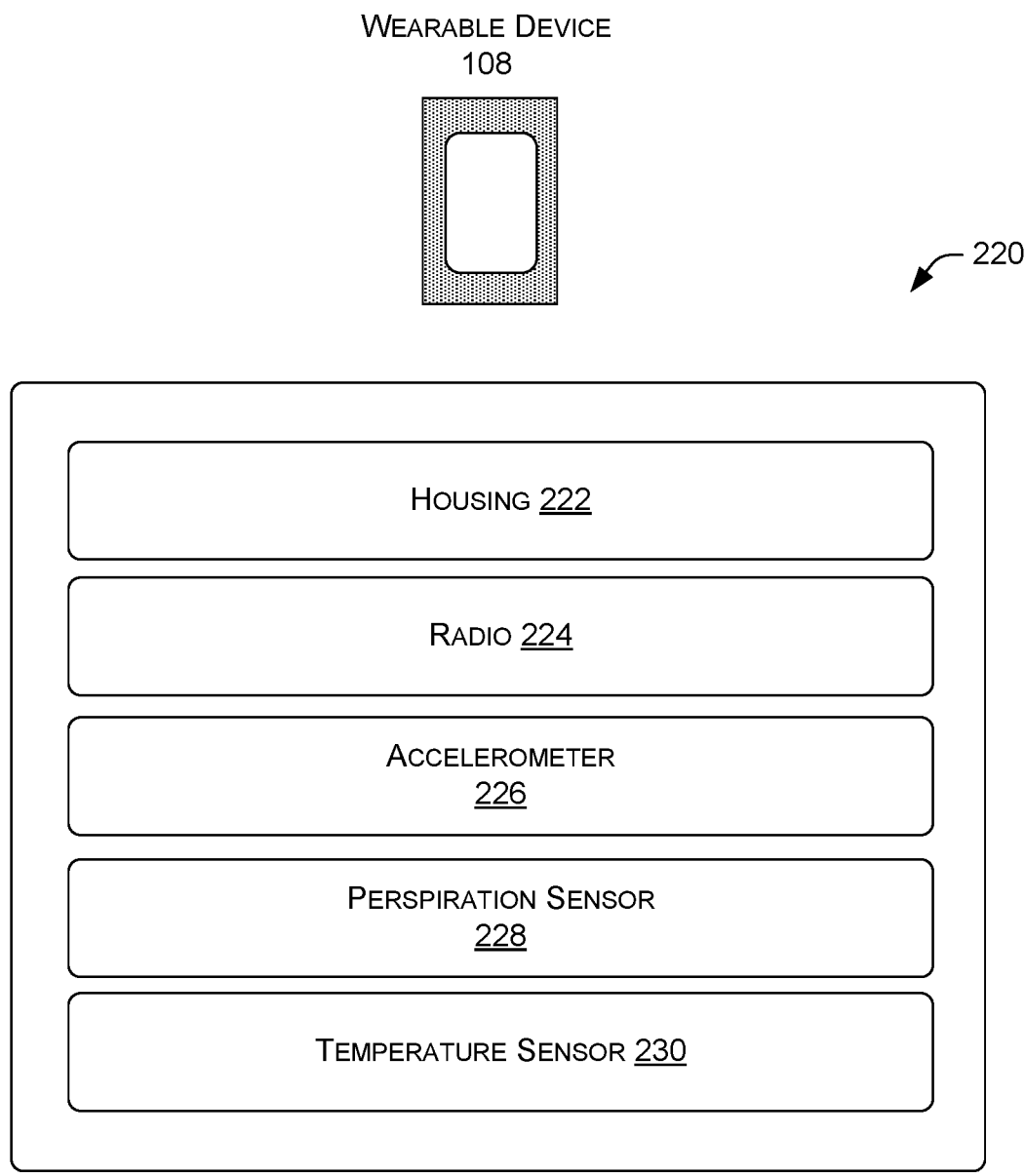
FIG. 2B is a block diagram of an illustrative architecture of an illustrative wearable device that may provide movement data to the analytic(s) device.

FIG. 2B is a block diagram of an illustrative architecture 240 of an illustrative wearable device that may provide movement data to the analytic(s) device. The architecture 240 may include at least some of a housing 222, a radio 224, an accelerometer 226, a perspiration sensor 228, and a temperature sensor 230. However, the architecture 240 may include other components, sensors, or devices, such as a power source (e.g., a battery), a motion sensor, a clock, a display, and/or other components.

The accelerometer 226 may be configured to provide output in up to 6-degrees of motion to define acceleration in three-dimensional space. In some embodiments, multiple accelerometers may be used in the architecture.

The radio 224 may provide output of data from the wearable device, which may be affixed to a user and/or equipment. The radio may output signals using standard radio protocols, such as Bluetooth®, Wi-Fi, near field communication, and so forth. In some embodiments, signals from the wearable device may be received by an intermediate device near the user, and then relayed to the analytics device, which may be located offsite such as when the analytics device is implemented in a cloud-services configurate at one or more remote locations different from the wearable device.

The perspiration sensor 228 may detect presence of perspiration and/or may measure an amount of perspiration for a given time. The temperature sensor 230 may include a thermocouple or other temperature sensor configured to measure a temperature of the user, such as a core temperature of the user or other temperatures of the user (e.g., skin temperature, etc.)

FIGS. 3-5 and 8 are flow diagrams of illustrative processes illustrated as a collection of blocks in a logical flow graph, which represent a sequence of operations that can be implemented in hardware, software, or a combination thereof. In the context of software, the blocks represent computer-executable instructions stored on one or more computer-readable storage media that, when executed by one or more processors, perform the recited operations. Generally, computer-executable instructions include routines, programs, objects, components, data structures, and the like that perform particular functions or implement particular abstract data types. The order in which the operations are described is not intended to be construed as a limitation, and any number of the described blocks can be combined in any order and/or in parallel to implement the processes.

Figure 3:
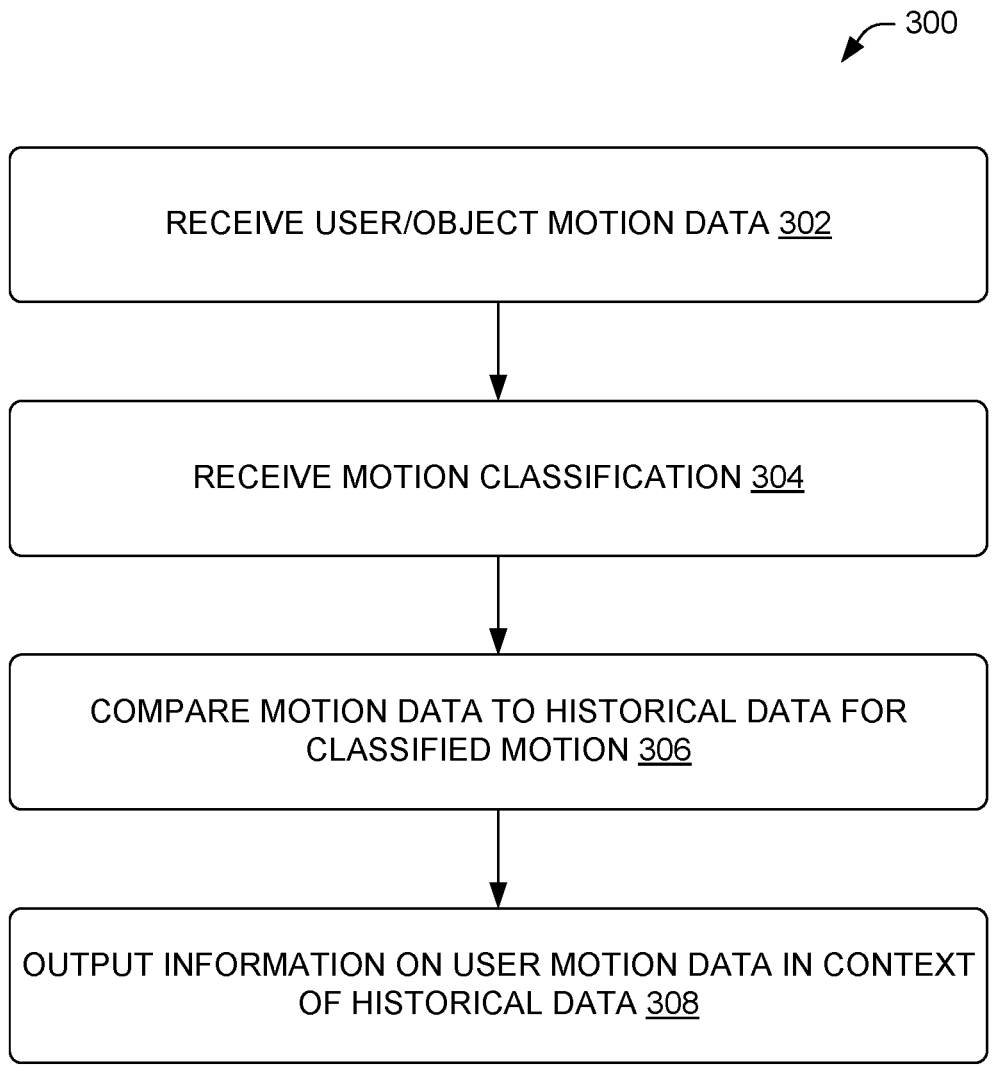
FIG. 3 is a flow diagram of an illustrative process to generation information from user motion data analyzed using streaming analytics.

FIG. 3 is a flow diagram of an illustrative process 300 to generate information from user motion data analyzed using streaming analytics. The process 300 is described with reference to the environment 100 and the computing architecture 200 and may be performed by the access management service. Of course, the process 300 may be performed in other similar and/or different environments.

At 302, the service 104 may receive motion data from a wearable device. The motion data may be accompanied by other user data, such as information about a state of the user's body temperature, perspiration, and/or other signals that indicate information about the user's body. The motion data may include signals from one or more accelerometers that indicate acceleration and direction of movement of the user over a period of time.

At 304, the service 104 may receive a motion classification associated with the motion data. The motion classification may describe a type of motion during the period of time associated with creation of the motion data received at the operation 302. The motion classification may be created by a user, may be crowdsourced, and/or may be created based on analysis of imagery of the user performing the motion during the period of time.

At 306, the service 104 may compare the user motion data to historical data for the classified motion. For example, the service 104 may utilize a ML model that is based on historical information to compare the user motion data for the particular classified motion to determine information about performance and/or other information or classification of the user's movement, such as an indication of an injury, fatigue, or a possible upcoming injury.

At 308, the service 104 may output information associated with the user motion data in context of the historical data, which may be incorporated in one or more ML models. For example, a ML model may predict that the user is injured and may output a message to describe the injury of the user to be evaluated by a person. The output may be based on prior injuries to the user or other users that correlate to similar trends in the motion data for the classified motion. As another example, the output may be a recommendation for a rest based on a measured level of fatigue. The recommendation may be scheduled or recommended for a time that is optimized by the ML model to provide optimized performance for the activity. For example, the output may indicate that a tennis player should take a rest at a certain time during a match.

Figure 4:
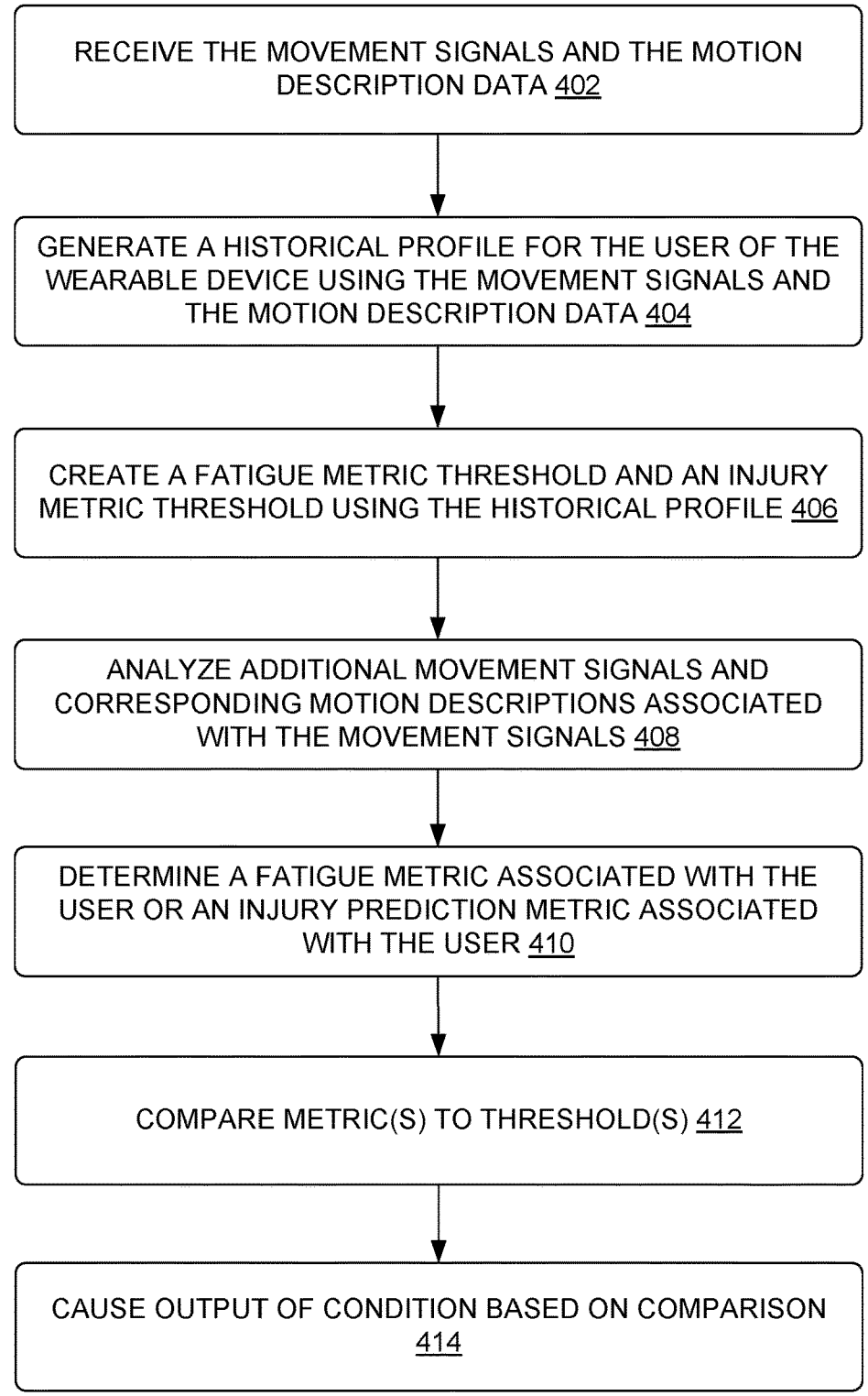
FIG. 4 is a flow diagram of an illustrative process to create motion profiles and perform analytics using the motion profiles.

FIG. 4 is a flow diagram of an illustrative process 400 to create motion profiles and perform analytics using the motion profiles. The process 400 is described with reference to the environment 100 and the computing architecture 200 and may be performed by the access management service. Of course, the process 400 may be performed in other similar and/or different environments.

At 402, the service 104 may receive movement signals and motion description data (e.g., motion classification). The movement signals may be received from a wearable device, possibly via an intermediary device that relays signals or data to the service 104.

At 404, the service 104 may generate a historical profile for the user of the wearable device using the movement signals and the motion description data. In some embodiments, the historical profile may be generated by a ML model or may be a ML model. For example, historical data may be used to create weights for one or more ML models associated with the movement described by the motion description data.

At 406, the service 104 may create a fatigue metric threshold and an injury metric threshold using the historical profile associated with the user. The thresholds may be incorporated in the ML model and may be used to initiate output of a message regarding an activity of the user.

At 408, the service 104 may analyze additional movement signals and corresponding motion descriptions associated with the movement signals. The additional movement signals may provide input to a ML model based on historical information and created and/or updated at the operation 404.

At 410, the service 104 may determine a fatigue metric associated with the user and/or an injury prediction metric associated with the user based on the additional movement signals analyzed at the operation 408. For example, a user may wear one or more wearable device while performing an activity (e.g., running a 40-yard sprint). Thresholds may indicate minimum or certain acceleration values that correlate with fatigue and/or injury prevention.

At 412, the service 104 may compare the metrics from the operation 410 to the thresholds from the operation 406, or otherwise leverage one or more ML model to determine a classification of the additional movement data based on the historical profile. For example, the service 104 may compare acceleration data from a current running of the 40-yard dash to historical values and threshold associated with the historical values. In some embodiments, specific movement data may be analyzed, such as a user's gait, which may upon analysis enable determination of an injury or a possibly injury if no corrective action is implemented, such as a rest or change of motion.

At 414, the service 104 may cause output of the condition based on the comparison. For example, the service 104 may send an output to a device associated with the user, to a teammate, to a trainer, to a coach, to a health profession, or to a device associated with another interested party approved by the user.

Figure 5:
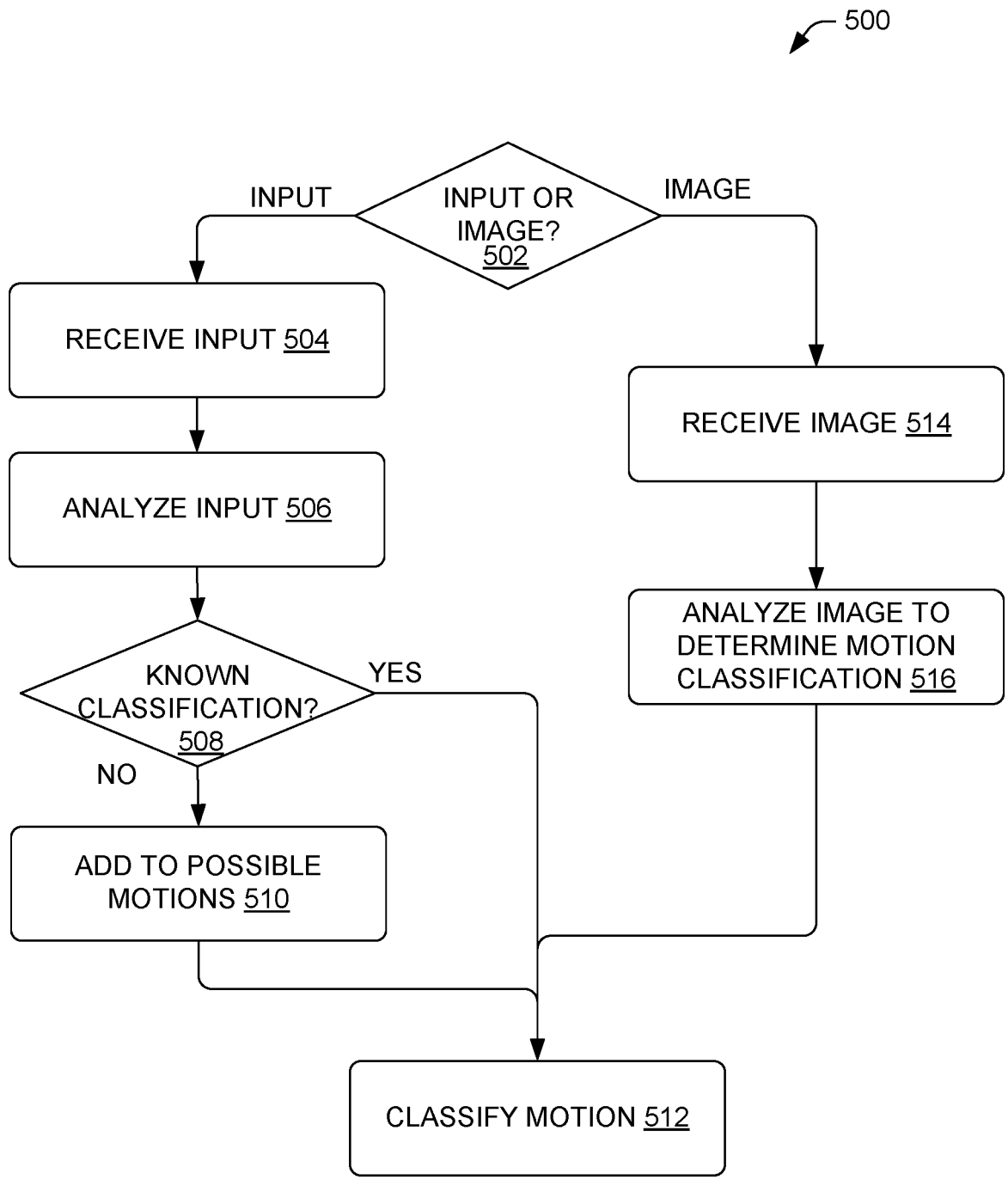
FIG. 5 is a flow diagram of an illustrative process to classify motion.

FIG. 5 is a flow diagram of an illustrative process 500 to classify motion. The process 500 is described with reference to the environment 100 and the computing architecture 200 and may be performed by the access management service. Of course, the process 500 may be performed in other similar and/or different environments.

At 502, the motion classifier 112 may determine whether information for a motion description is created by input (text, audio) or by imagery. When the information for a motion description is created by an input (following the "input" route from the decision operation 502), then the process 500 may advance to an operation 504.

At 504, the motion classifier 112 may receive the input. The input may be received in response to a direct input of the motion description or by input of other information that includes the motion description. For example, the input may be from a play caller, a radio broadcast, a written play-by-play blog, and/or other inputs.

At 506, the input may be analyzed to determine the motion description. In some embodiments, audio may be converted to text as part of the analysis. In various embodiments, text may be analyzed to locate and classify the motion description in accordance with known movement classifications 118 shown in FIG. 1.

At 508, the motion classifier 112 may determine if the motion description is a known classification from the movement classifications 118. When the motion description is not a known classification, but is a valid classification, such as a new play, a new action, a new activity, etc., (following the "no" route from the decision operation 508), then the process may advance to an operation 510. At 510, the motion classifier 112 may add the new motion description to the movement classifications 118.

When the motion description is a known classification (following the "yes" route from the decision operation 508), or following the operation 510, then the process may advance to an operation 512. At 512, the movement may be classified by data, which may be transmitted in association with signal from a wearable device, for example.

When the information for a motion description is created by an image (following the "image" route from the decision operation 502), then the process 500 may advance to an operation 514. At 514, the motion classifier 112 may receive imagery, such as a still image or video of the user performing movement used to generate movement signals via a wearable device.

At 516, the motion classifier 112 may use image analysis algorithms to analyze the imagery to classify the motion. For example, a video of a football play may be analyzed to determine a name of an offensive play, including a movement of a specific player (e.g., a wide receiver, etc.). This may be used to determine the movement description. Following the operation 514, the motion may be classified at the operation 512.

FIGS. 6A-D show illustrative graphs showing example body movements and corresponding illustrative threshold data.

Figure 6A:
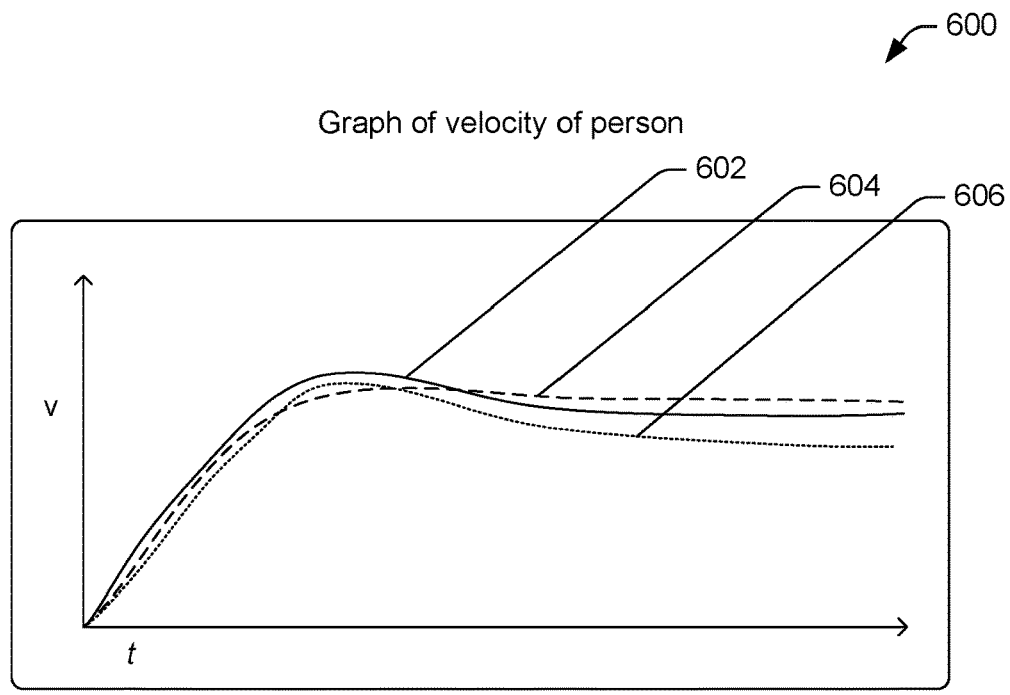
FIGS. 6A-D show illustrative graphs showing example body movements and corresponding illustrative threshold data.

FIG. 6A shows a first graph 600 that includes metrics plotted by time (x-axis) and velocity (v) (y-axis) where the metrics are from a wearable device worn by a user and the metrics represent user motion and/or activity. The first graph 600 may include first data 602 representing performance of an action during a first scenario, such as a during a game. The first graph 600 may include second data 604 representing performance of the action during a second scenario, such as a during a practice. The first data 602 may be slightly different than the second data 604, which may be explained by the scenario. Thus, data may be classified by a type of scenario to include these differences in the data, such as in the ML model(s), thresholds, weights, and so forth. The first graph 600 may include third data 606 representing a threshold performance. For example, when actual performance is below the threshold performance, the service 104 may output a message and/or a recommendation. The threshold may be indicative of fatigue, an injury, or a possibly future injury, for example. The recommendation may include a rest, a change in the activity, hydration, and/or other recommendations.

In various embodiments, the practice data may be used to create different weights as compared to game or non-practice data. For example, the system may classify at least some data of movement data as practice movement and other data of the movement data as game movement, and may apply a first weight to the practice movement and a second, different weight to the game movement. The weighs may be used by the ML model and/or to determine thresholds for the movement data as discussed above.

Figure 6B:
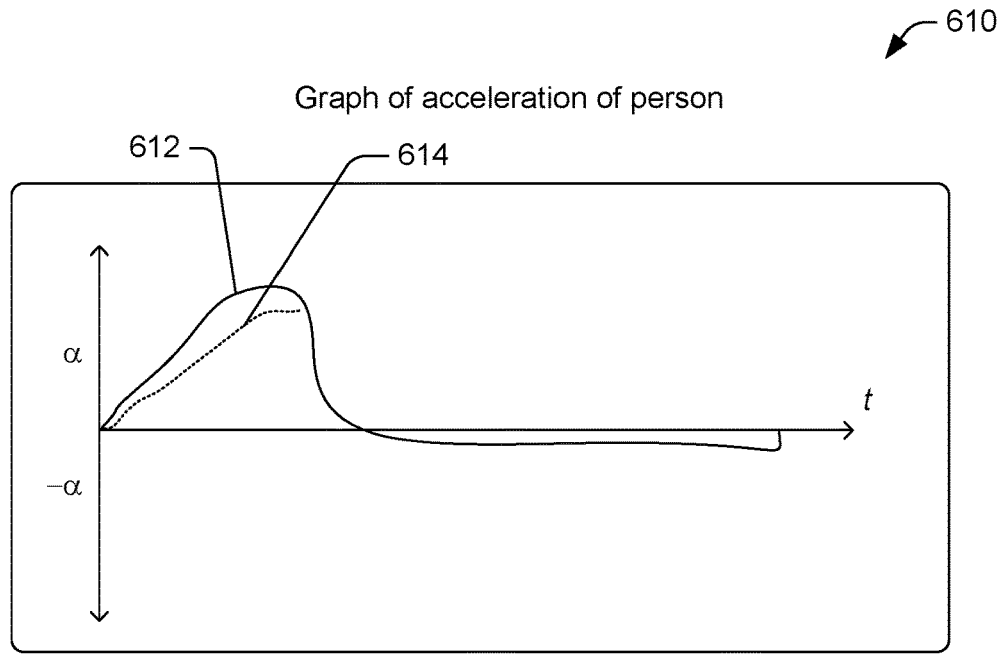

FIG. 6B shows a second graph 610 that represents the action shown in FIG. 6A, but plotted with respect to acceleration on the y-axis. The second graph 610 may include fourth data 612 which may be acceleration data from the movement represented in the first action 602. The acceleration data may be generated one or more accelerometers included in a wearable device. The second graph 610 may include fifth data 612 which may be threshold performance for the acceleration. For example, when actual performance is below the threshold performance, the service 104 may output a message and/or a recommendation. The threshold may be indicative of fatigue, an injury, or a possibly future injury, for example. The recommendation may include a rest, a change in the activity, hydration, and/or other recommendations.

Figure 6C:
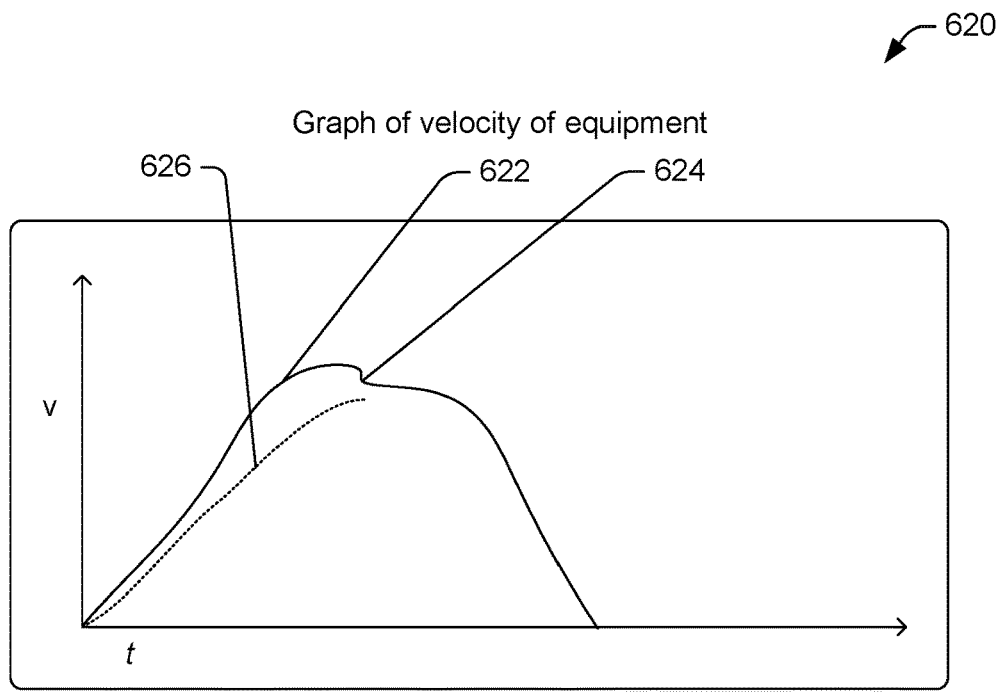

FIG. 6C shows a third graph 620 that includes metrics plotted by time (x-axis) and velocity (v) (y-axis) where the metrics are from equipment used by a user during an activity and the metrics represent equipment motion and/or activity. In this example, sixth data 622 represents motion of a racquet and striking of an object at 624, such as a ball. The third graph 620 may include seventh data 626 representing a threshold performance. For example, when actual performance is below the threshold performance, the service 104 may output a message and/or a recommendation. The threshold may be indicative of fatigue, an injury, or a possibly future injury, for example. The recommendation may include a rest, a change in the activity, hydration, and/or other recommendations.

Figure 6D:
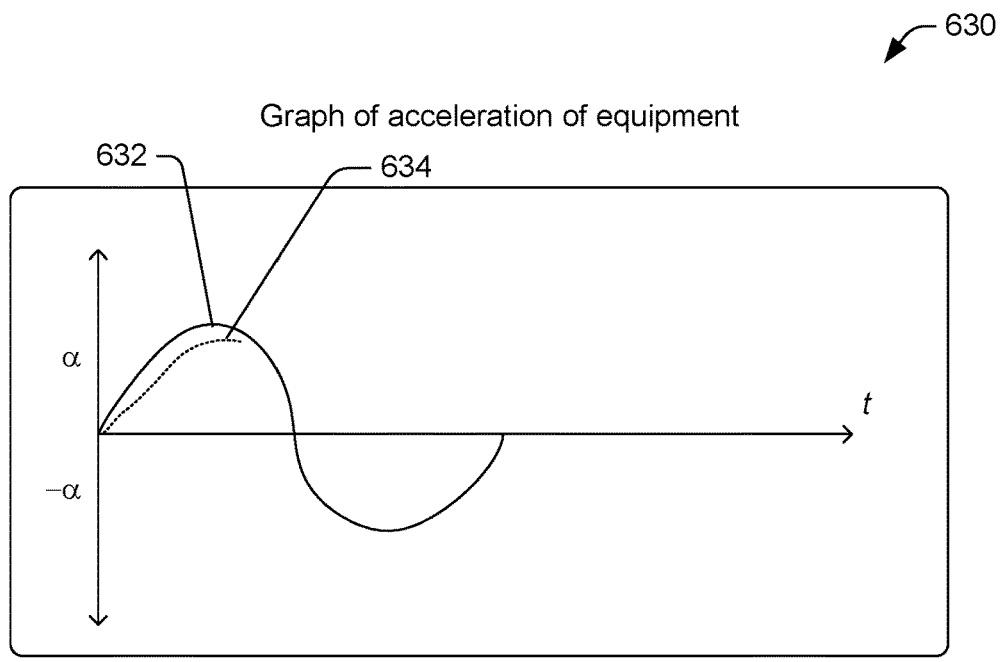

FIG. 6D shows a fourth graph 630 that represents the action shown in FIG. 6C, but plotted with respect to acceleration on the y-axis. The fourth graph 630 may include eighth data 632 which may be acceleration data from the movement represented in the action of the equipment. The acceleration data may be generated one or more accelerometers included in the equipment. The fourth graph 630 may include ninth data 634 which may be threshold performance for the acceleration. For example, when actual performance is below the threshold performance, the service 104 may output a message and/or a recommendation. The threshold may be indicative of fatigue, an injury, or a possibly future injury, for example. The recommendation may include a rest, a change in the activity, hydration, and/or other recommendations.

In some embodiments, ML model(s) may utilize inputs from wearable devices worn by users and by wearable devices included in equipment, such as racquets, clothing, pads, and/or other equipment used in an activity, such as a sports activity, a work activity, or other activities.

Figure 7:
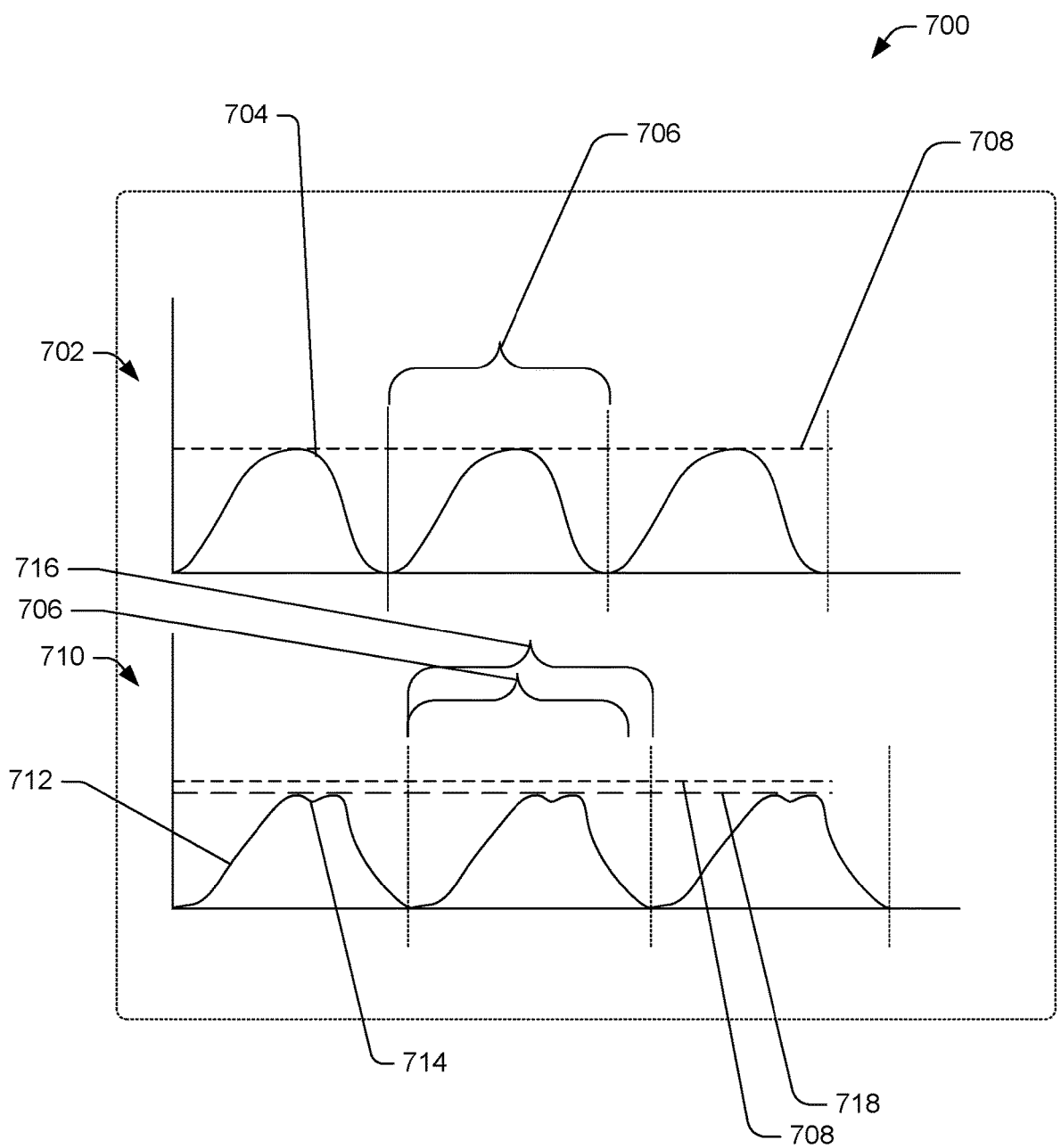
FIG. 7 shows an illustrative graph showing a motion profile with thresholds in comparison to a current motion of a user.

FIG. 7 shows an illustrative graph 700 showing a motion profile with thresholds in comparison to a current motion of a user. A first graph 702 shows baseline motion data 704, which may represent certain human body movement measured by a wearable device, such as a user's gait. The motion data 704 may include attributes such as a baseline phase 706 and/or a baseline peak 708. This information may be used for comparison to other movement data, possibly using a ML model.

The graph 700 includes a second graph 710 representing current motion data 712. The current motion data 712 may include motion of a same activity as the baseline motion data 704, and may be compared to the baseline motion data 704 to determine attributes of the user, such as fatigue, incorrect movement, an injury, a possibility of a future injury, and/or other information. For example, the baseline motion data 704 may represent proper movement of a physical therapy activity while the current motion data 712 may represent the user's attempt to perform the physical therapy activity, which may not be correct, and thus may not be an exact duplicate or mirror image of the baseline motion data 704.

The current motion data 712 may include attributes such as variations 714 that are not included in the baseline motion data 704, a current phase 716, and/or a current peak 718. The attributes, when compared to historical information directly or via a ML model(s), may provide information to classify the current motion, possibly as indicating fatigue, injury, an incorrect movement. The output may be a score or percent to indicate a degree of variation between the current motion data 712 and the baseline motion data 704. Of course, other comparisons may be made using the baseline motion data 704 and the current motion data 712.

Figure 8:
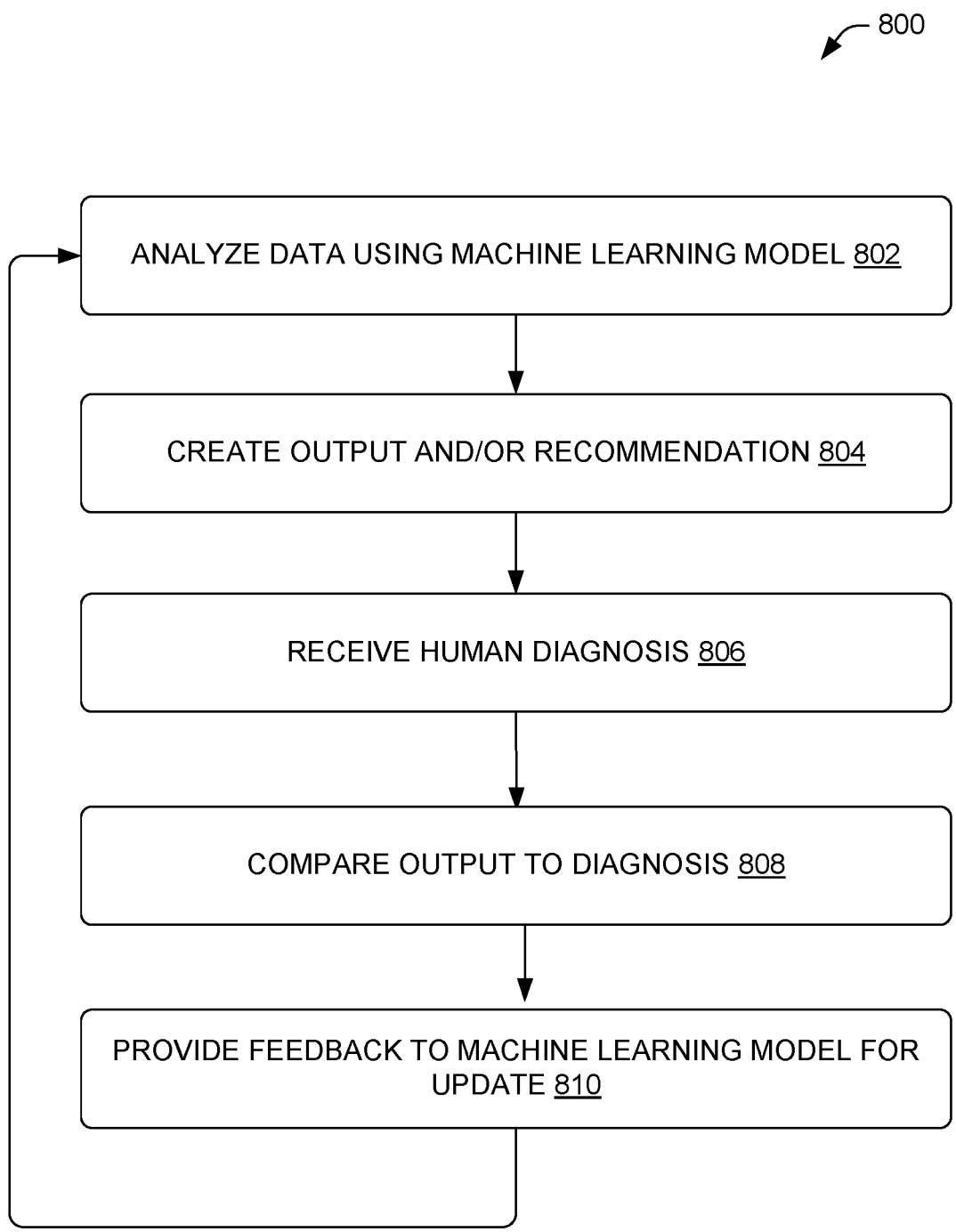
FIG. 8 is a flow diagram of an illustrative process to receive feedback to update a learning model.

FIG. 8 is a flow diagram of an illustrative process 800 to receive feedback to update a learning model. The process 800 is described with reference to the environment 100 and the computing architecture 200 and may be performed by the access management service. Of course, the process 800 may be performed in other similar and/or different environments.

At 802, the service 104 may analyze data using a ML model to create an output. For example, the service 104 may analyze user motion data and create an output of a predicted injury of the user.

At 804, the service 104 may create an output and/or recommendation. For example, the output may be a notification of the injury of the user.

At 806, the service 104 may receive an input following human diagnosis of the user that may be performed in response to the output from the operation 804. For example, an athletic trainer may evaluate the person who performed the movement measured by the service via the operation 802.

At 808, the service 104 may determine whether the prediction (or output) was correct based on a comparison of the output and the diagnosis input received at the operation 806. This comparison may be used to update the ML model.

AT 810, the service 104 may update the ML model based on the comparison from the operation 808. For example, if the prediction was incorrect (e.g., the prediction was different than the diagnosis), then the service 104 may update the ML model in first way, such as by changing one or more weights and/or threshold values used by the machine learning system and/or using the data and correct output as additional training data. If the prediction is correct, this could also be used to update the ML model in a similar way.

Figure 9:
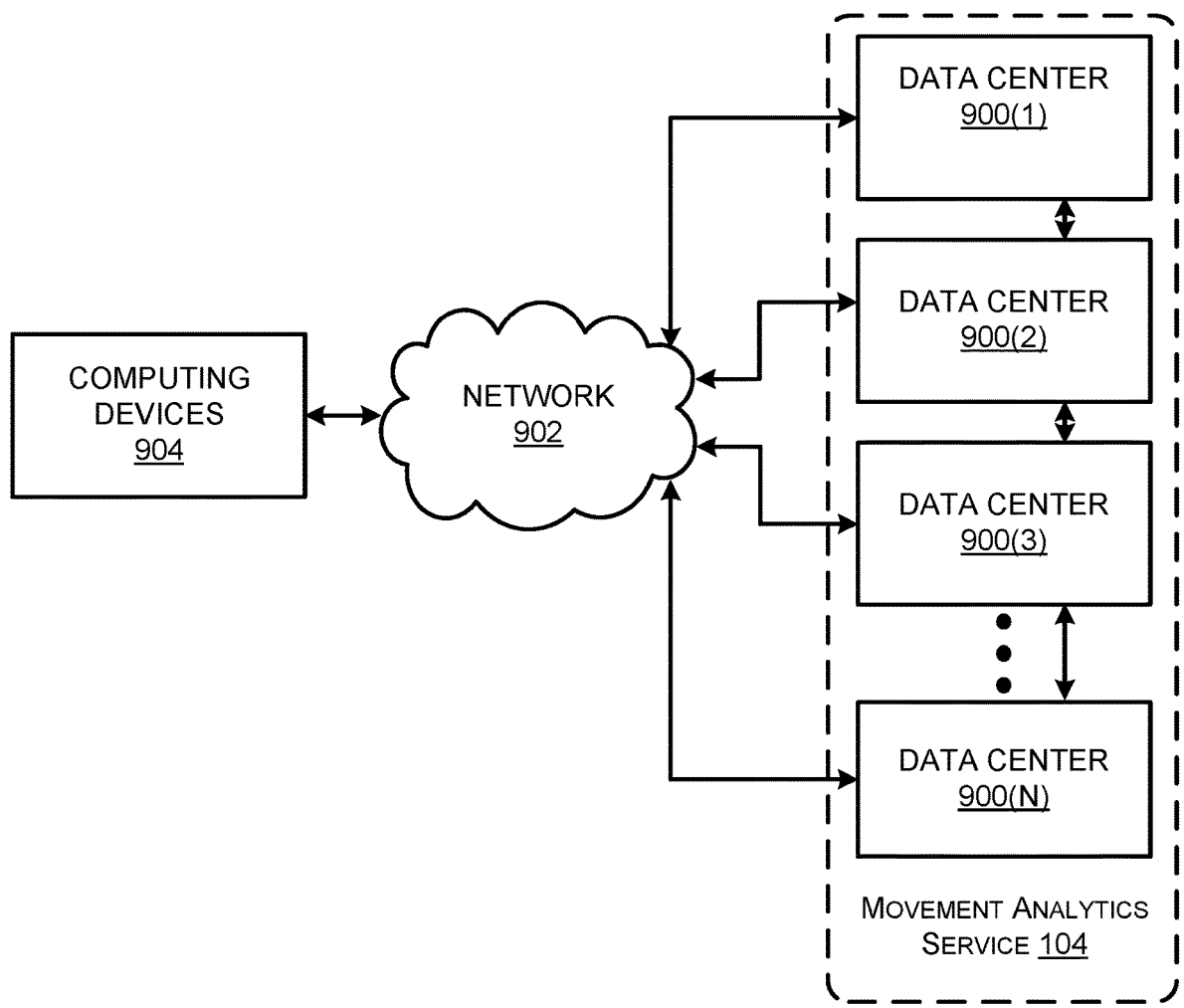
FIG. 9 is a system and network diagram that shows an illustrative operating environment that includes a system that can be configured to implement aspects of the functionality described herein.

FIG. 9 is a system and network diagram that shows an illustrative operating environment that includes a system, such as the that can be configured to implement aspects of the functionality described herein of the movement analytics service 104. As discussed briefly above, the system can execute network services, such as the data storage and data streaming, and/or provide computing resources, such as for the concentrator, on a permanent or an as-needed basis. Among other types of functionality, the computing resources provided by the system, or by a larger system of which the system is a part, can be utilized to implement the various network services described herein. As also discussed above, the system may be part of a larger system that provides the additional computing resources that include, without limitation, data storage resources, data processing resources, such as virtual machine (VM) instances, networking resources, data communication resources, network services, and other types of resources.

Each type of computing resource provided by system, or by a larger system of which the system is a part, can be general-purpose or can be available in a number of specific configurations. For example, data processing resources can be available as physical computers or VM instances in a number of different configurations. The VM instances can be configured to execute applications, including web servers, application servers, media servers, database servers, some or all of the network services described above, and/or other types of programs. Data storage resources can include file storage devices, block storage devices, and the like. The system, or a larger system of which the system is a part, can also be configured to provide other types of computing resources not mentioned specifically herein.

The computing resources provided by system, or a larger system of which the system is a part, are enabled in one implementation by one or more data centers 900(1), 900(2), 900(3), ..., 900(N). The data centers are facilities utilized to house and operate computer systems and associated components. The data centers typically include redundant and backup power, communications, cooling, and security systems. The data centers can also be located in geographically disparate locations. One illustrative configuration for a data center that can be utilized to implement the technologies disclosed herein will be described below with regard to FIG. 10.

The users of the system can access the computing resources, such as AMS 102, provided by the system over a network 902, which can be a wide area communication network ("WAN"), such as the Internet, an intranet or an Internet service provider ("ISP") network or a combination of such networks. For example, and without limitation, a computing device 904 operated by a user of the system can be utilized to access the system by way of the network 902. It should be appreciated that a local-area network ("LAN"), the Internet, or any other networking topology known in the art that connects the data centers to remote users and other users can be utilized. It should also be appreciated that combinations of such networks can also be utilized.

Figure 10:
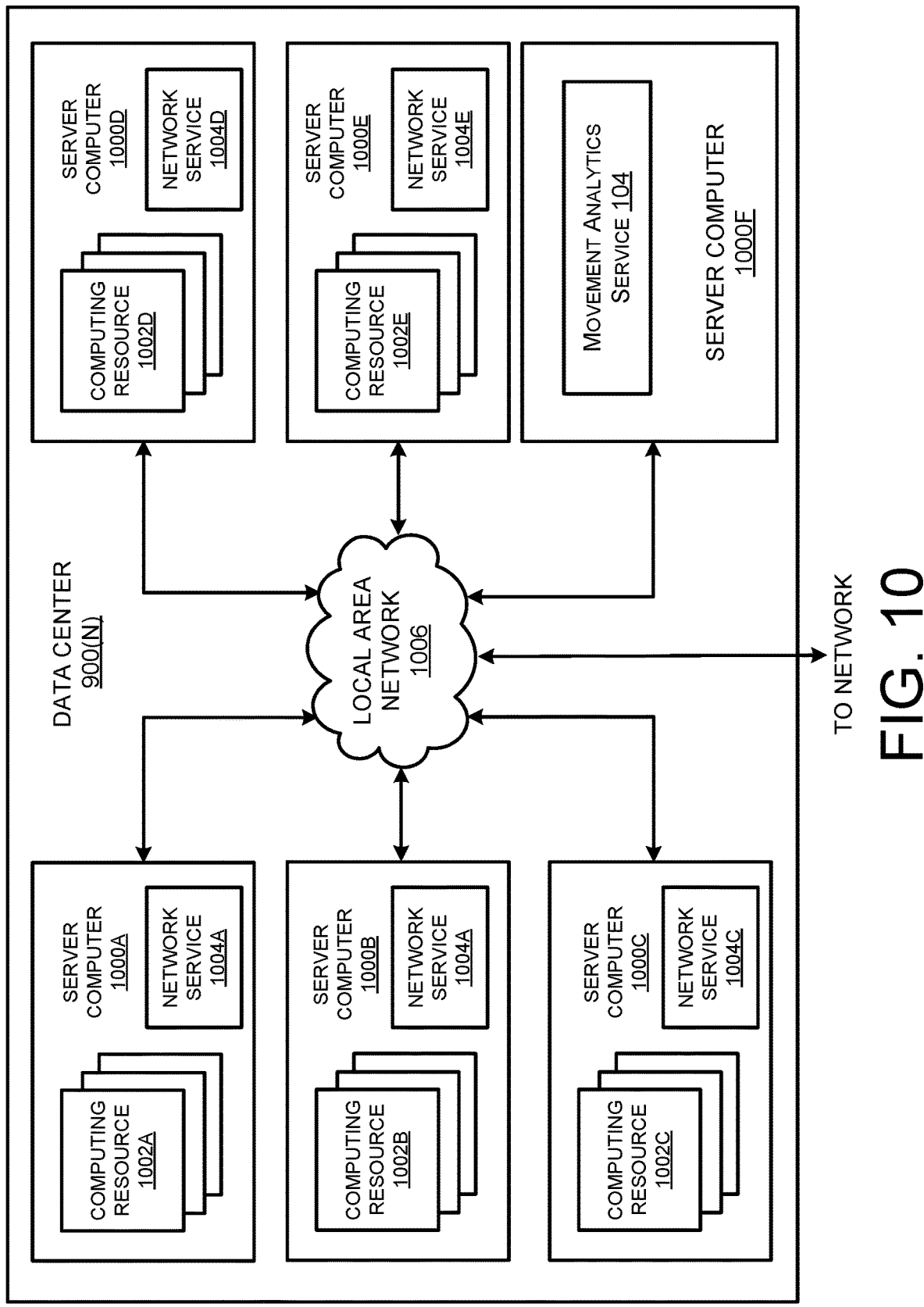
FIG. 10 is a computing system diagram illustrating a configuration for a data center that can be utilized to implement aspects of the technologies disclosed herein.

FIG. 10 is a computing system diagram that illustrates one configuration for a data center 900(N) that can be utilized to implement the AMS 102 as described above in FIGS. 1-8, and/or any other network services disclosed herein, such as the computing instance 106 and/or the access manager 108. The example data center 900(N) shown in FIG. 10 includes several server computers 1000A-1000E (collectively 1000) for providing the computing resources 1002A-1002E (collectively 1002), respectively.

The server computers 1000 can be standard tower, rack-mount, or blade server computers configured appropriately for providing the various computing resources described herein (illustrated in FIG. 10 as the computing resources 1002A-1002E). As mentioned above, the computing resources 1002 provided by the system, or a larger system of which the system is a part, can include, without limitation, analytics applications, data storage resources, data processing resources such as VM instances or hardware computing systems, database resources, networking resources, and others. Some of the servers 1000 can also be configured to execute network services 1004A-1004E (collectively 1004) capable of instantiating, providing and/or managing the computing resources 1002, some of which are described in detail herein.

The data center 900(N) shown in FIG. 10 also includes a server computer 1000F that can execute some or all of the software components described above. For example, and without limitation, the server computer 1000F can be configured to execute the AMS 102. The server computer 1000F can also be configured to execute other components and/or to store data for providing some or all of the functionality described herein. In this regard, it should be appreciated that components or different instances of the AMS 102 can execute on many other physical or virtual servers in the data centers 800 in various configurations.

In the example data center 900(N) shown in FIG. 10, an appropriate LAN 1006 is also utilized to interconnect the server computers 1000A-1000F. The LAN 1006 is also connected to the network 902 illustrated in FIG. 9. It should be appreciated that the configuration of the network topology described herein has been greatly simplified and that many more computing systems, software components, networks, and networking devices can be utilized to interconnect the various computing systems disclosed herein and to provide the functionality described above.

Appropriate load balancing devices or other types of network infrastructure components can also be utilized for balancing a load between each of the data centers 900(1)-(N), between each of the server computers 1000A-1000F in each data center 900, and, potentially, between computing resources 1002 in each of the data centers 900. It should be appreciated that the configuration of the data center 800 described with reference to FIG. 10 is merely illustrative and that other implementations can be utilized.

Figure 11:
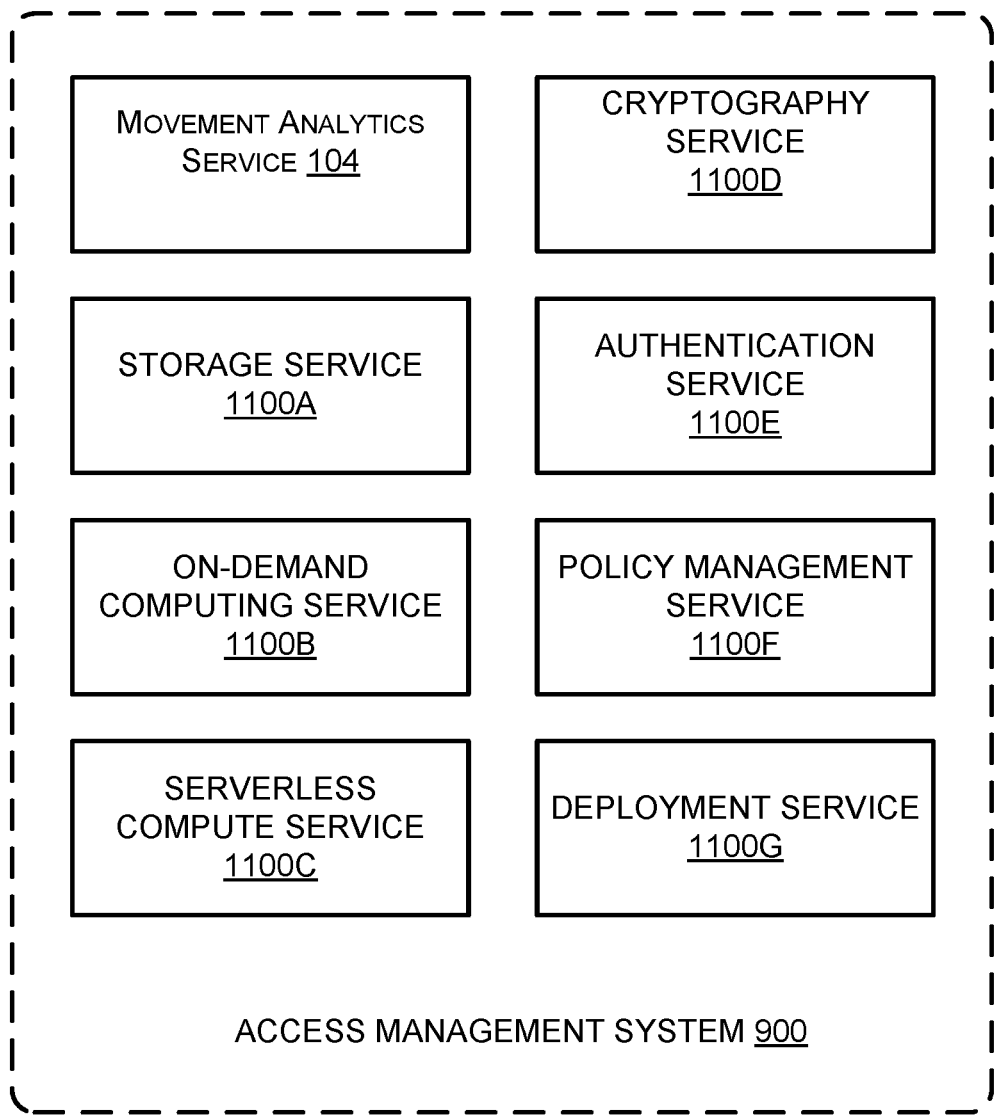
FIG. 11 is a network services diagram that shows aspects of several services that can be provided by and utilized within a system, or a larger system of which the system is a part, which is configured to implement the various technologies disclosed herein.

FIG. 11 is a network services diagram that shows aspects of several services that can be provided by and utilized within the system, or a larger system of which the system is a part, which is configured to implement the various technologies disclosed herein. In particular, and as discussed above, the system, or a larger system of which the system is a part, can provide a variety of network services to users and other users including, but not limited to, the service 104 and/or the computing instance 106, a storage service 1100A, an on-demand computing service 1100B, a serverless compute service 1100C, a cryptography service 1100D, an authentication service 1100E, a policy management service 1100F, and a deployment service 1100G. The system, or a larger system of which the system is a part, can also provide other types of network services, some of which are described below.

It is also noted that not all configurations described include the network services shown in FIG. 11 and that additional network services can be provided in addition to, or as an alternative to, the services explicitly described herein. Each of the services shown in FIG. 11 can also expose web service interfaces that enable a caller to submit appropriately configured API calls to the various services through web service requests. The various web services can also expose GUIs, command line interfaces ("CLIs"), and/or other types of interfaces for accessing the functionality that they provide. In addition, each of the services can include service interfaces that enable the services to access each other. Additional details regarding some of the services shown in FIG. 11 will now be provided.

The storage service 1100A can be a network-based storage service that stores data obtained from users of the system, or a larger system of which the system is a part. The data stored by the storage service 1100A can be obtained from computing devices of users.

The on-demand computing service 1100B can be a collection of computing resources configured to instantiate VM instances and to provide other types of computing resources on demand. For example, a user of the system, or a larger system of which the system is a part, can interact with the on-demand computing service 1100B (via appropriately configured and authenticated API calls, for example) to provision and operate VM instances that are instantiated on physical computing devices hosted and operated by the system, or a larger system of which the system is a part. The VM instances can be used for various purposes, such as to operate as servers supporting the network services described herein, a web site, to operate business applications or, generally, to serve as computing resources for the user.

Other applications for the VM instances can be to support database applications, electronic commerce applications, business applications and/or other applications. Although the on-demand computing service 1100B is shown in FIG. 11, any other computer system or computer system service can be utilized in the system, or a larger system of which the system is a part, to implement the functionality disclosed herein, such as a computer system or computer system service that does not employ virtualization and instead provisions computing resources on dedicated or shared computers/servers and/or other physical devices.

The serverless compute service 1100C is a network service that allows users to execute code (which might be referred to herein as a "function") without provisioning or managing server computers in the system, or a larger system of which the system is a part. Rather, the serverless compute service 1100C can automatically run code in response to the occurrence of events. The code that is executed can be stored by the storage service 1100A or in another network accessible location.

In this regard, it is to be appreciated that the term "serverless compute service" as used herein is not intended to infer that servers are not utilized to execute the program code, but rather that the serverless compute service 1100C enables code to be executed without requiring a user to provision or manage server computers. The serverless compute service 1100C executes program code only when needed, and only utilizes the resources necessary to execute the code. In some configurations, the user or entity requesting execution of the code might be charged only for the amount of time required for each execution of their program code.

The system, or a larger system of which the system is a part, can also include a cryptography service 1100D. The cryptography service 1100D can utilize storage services of the system, or a larger system of which the system is a part, such as the storage service 1100A, to store encryption keys in encrypted form, whereby the keys can be usable to decrypt user keys accessible only to particular devices of the cryptography service 1100D. The cryptography service 1100D can also provide other types of functionality not specifically mentioned herein.

The system, or a larger system of which the system is a part, in various configurations, also includes an authentication service 1100E and a policy management service 1100F. The authentication service 1100E, in one example, is a computer system (i.e., collection of computing resources 1002) configured to perform operations involved in authentication of users or customers. For instance, one of the services shown in FIG. 11 can provide information from a user or customer to the authentication service 1100E to receive information in return that indicates whether or not the requests submitted by the user or the customer are authentic.

The policy management service 1100F, in one example, is a network service configured to manage policies on behalf of users or customers of the system, or a larger system of which the system is a part. The policy management service 1100F can include an interface (e.g. API or GUI) that enables customers to submit requests related to the management of policy, such as a security policy. Such requests can, for instance, be requests to add, delete, change or otherwise modify policy for a customer, service, or system, or for other administrative actions, such as providing an inventory of existing policies and the like.

The system, or a larger system of which the system is a part, can additionally maintain other network services based, at least in part, on the needs of its customers. For instance, the system, or a larger system of which the system is a part, can maintain a deployment service 1100G for deploying program code in some configurations. The deployment service 1100G provides functionality for deploying program code, such as to virtual or physical hosts provided by the on-demand computing service 1100B. Other services include, but are not limited to, database services, object-level archival data storage services, and services that manage, monitor, interact with, or support other services. The system, or a larger system of which the system is a part, can also be configured with other network services not specifically mentioned herein in other configurations.

Figure 12:
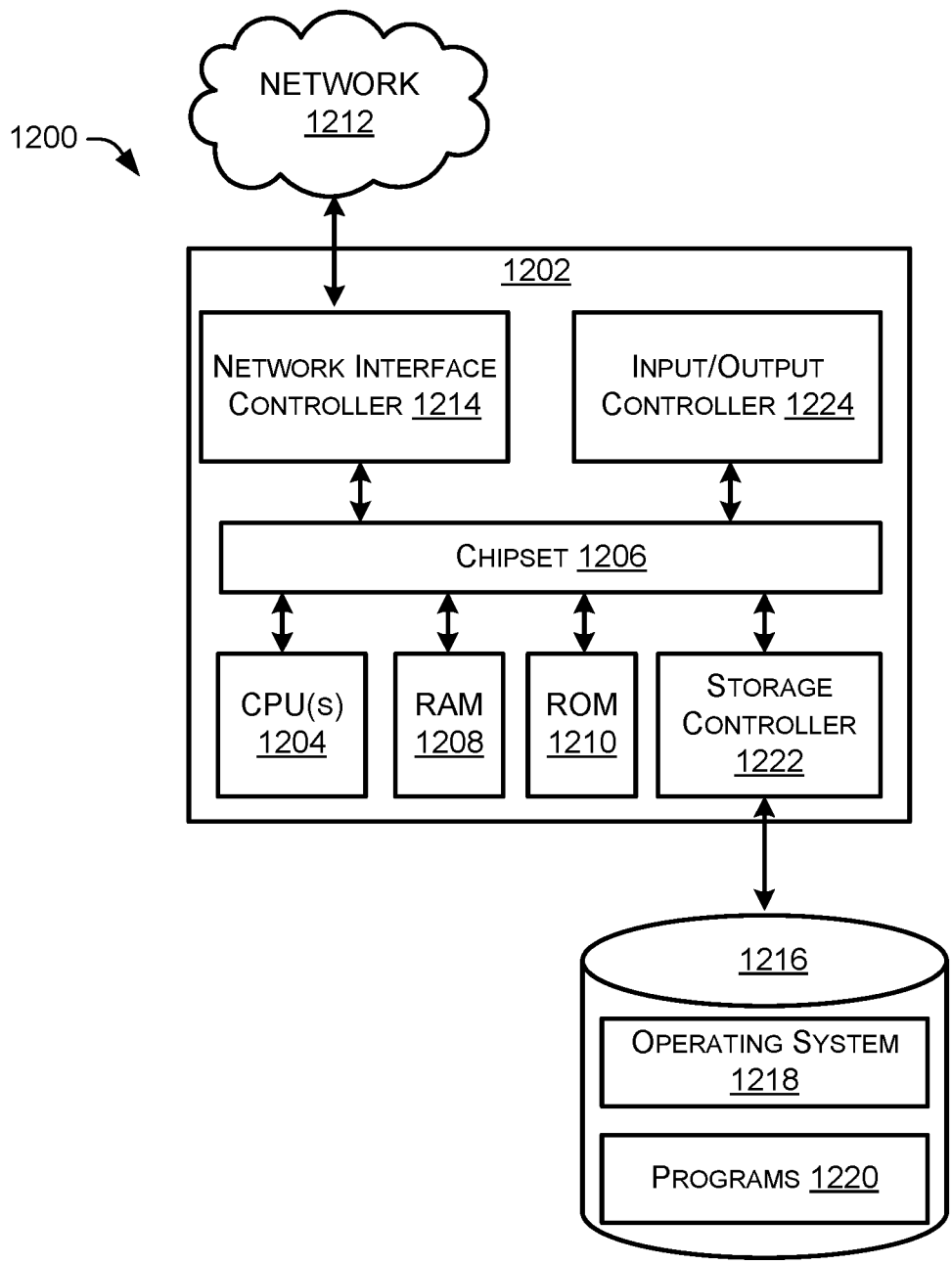
FIG. 12 is a computer architecture diagram showing an illustrative computer hardware architecture for implementing a computing device that can be utilized to implement aspects of the various technologies presented herein.

FIG. 12 shows an example computer architecture for a computer 1200 capable of executing program components for implementing the functionality described above. The computer architecture shown in FIG. 12 illustrates a conventional server computer, workstation, desktop computer, laptop, tablet, network appliance, e-reader, smartphone, or other computing device, and can be utilized to execute any of the software components presented herein. The computer 1200 may represent architecture for a naming service, a concentrator, a reader, and/or other devices described herein.

The computer 1200 includes a baseboard 1202, or "motherboard," which is a printed circuit board to which a multitude of components or devices can be connected by way of a system bus or other electrical communication paths. In one illustrative configuration, one or more central processing units ("CPUs") 1204 operate in conjunction with a chipset 1206. The CPUs 1204 can be standard programmable processors that perform arithmetic and logical operations necessary for the operation of the computer 1200.

The CPUs 1204 perform operations by transitioning from one discrete, physical state to the next through the manipulation of switching elements that differentiate between and change these states. Switching elements can generally include electronic circuits that maintain one of two binary states, such as flip-flops, and electronic circuits that provide an output state based on the logical combination of the states of one or more other switching elements, such as logic gates. These basic switching elements can be combined to create more complex logic circuits, including registers, adders-subtractors, arithmetic logic units, floating-point units, and the like.

The chipset 1206 provides an interface between the CPUs 1204 and the remainder of the components and devices on the baseboard 1202. The chipset 1206 can provide an interface to a RAM 1208, used as the main memory in the computer 1200. The chipset 1206 can further provide an interface to a computer-readable storage medium such as a read-only memory ("ROM") 1210 or non-volatile RAM ("NVRAM") for storing basic routines that help to startup the computer 1200 and to transfer information between the various components and devices. The ROM 1210 or NVRAM can also store other software components necessary for the operation of the computer 1200 in accordance with the configurations described herein.

The computer 1200 can operate in a networked environment using logical connections to remote computing devices and computer systems through a network, such as the network 1212. The chipset 1206 can include functionality for providing network connectivity through a NIC 1214, such as a gigabit Ethernet adapter. The NIC 1214 is capable of connecting the computer 1200 to other computing devices over the network 1212. It should be appreciated that multiple NICs 1214 can be present in the computer 1200, connecting the computer to other types of networks and remote computer systems.

The computer 1200 can be connected to a mass storage device 1216 that provides non-volatile storage for the computer. The mass storage device 1216 can store an operating system 1218, programs 1220, and data, which have been described in greater detail herein. The mass storage device 1216 can be connected to the computer 1200 through a storage controller 1222 connected to the chipset 1206. The mass storage device 1216 can consist of one or more physical storage units. The storage controller 1222 can interface with the physical storage units through a serial attached SCSI ("SAS") interface, a serial advanced technology attachment ("SATA") interface, a fiber channel ("FC") interface, or other type of interface for physically connecting and transferring data between computers and physical storage units.

The computer 1200 can store data on the mass storage device 1216 by transforming the physical state of the physical storage units to reflect the information being stored. The specific transformation of physical state can depend on various factors, in different implementations of this description. Examples of such factors can include, but are not limited to, the technology used to implement the physical storage units, whether the mass storage device 1216 is characterized as primary or secondary storage, and the like.

For example, the computer 1200 can store information to the mass storage device 1216 by issuing instructions through the storage controller 1222 to alter the magnetic characteristics of a particular location within a magnetic disk drive unit, the reflective or refractive characteristics of a particular location in an optical storage unit, or the electrical characteristics of a particular capacitor, transistor, or other discrete component in a solid-state storage unit. Other transformations of physical media are possible without departing from the scope and spirit of the present description, with the foregoing examples provided only to facilitate this description. The computer 1200 can further read information from the mass storage device 1216 by detecting the physical states or characteristics of one or more particular locations within the physical storage units.

In addition to the mass storage device 1216 described above, the computer 1200 can have access to other computer-readable storage media to store and retrieve information, such as program modules, data structures, or other data. It should be appreciated by those skilled in the art that computer-readable storage media is any available media that provides for the non-transitory storage of data and that can be accessed by the computer 1200.

By way of example, and not limitation, computer-readable storage media can include volatile and non-volatile, removable and non-removable media implemented in any method or technology. Computer-readable storage media includes, but is not limited to, RAM, ROM, erasable programmable ROM ("EPROM"), electrically-erasable programmable ROM ("EEPROM"), flash memory or other solid-state memory technology, compact disc ROM ("CD-ROM"), digital versatile disk ("DVD"), high definition DVD ("HD-DVD"), BLU-RAY, or other optical storage, magnetic cassettes, magnetic tape, magnetic disk storage or other magnetic storage devices, or any other medium that can be used to store the desired information in a non-transitory fashion.

As mentioned briefly above, the mass storage device 1216 can store an operating system 1218 utilized to control the operation of the computer 1200. According to one configuration, the operating system comprises the LINUX operating system or one of its variants such as, but not limited to, UBUNTU, DEBIAN, and CENTOS. According to another configuration, the operating system comprises the WINDOWS SERVER operating system from MICROSOFT Corporation. According to further configurations, the operating system can comprise the UNIX operating system or one of its variants. It should be appreciated that other operating systems can also be utilized. The mass storage device 1216 can store other system or application programs and data utilized by the computer 1200.

In one configuration, the mass storage device 1216 or other computer-readable storage media is encoded with computer-executable instructions which, when loaded into the computer 1200, transform the computer from a general-purpose computing system into a special-purpose computer capable of implementing the configurations described herein. These computer-executable instructions transform the computer 1200 by specifying how the CPUs 1204 transition between states, as described above. According to one configuration, the computer 1200 has access to computer-readable storage media storing computer-executable instructions which, when executed by the computer 1200, perform the various processes described above. The computer 1200 can also include computer-readable storage media for performing any of the other computer-implemented operations described herein.

The computer 1200 can also include one or more input/output controllers 1224 for receiving and processing input from a number of input devices, such as a keyboard, a mouse, a touchpad, a touch screen, an electronic stylus, or other type of input device. Similarly, an input/output controller 1224 can provide output to a display, such as a computer monitor, a flat-panel display, a digital projector, a printer, or other type of output device. It will be appreciated that the computer 1200 might not include all of the components shown in FIG. 12, can include other components that are not explicitly shown in FIG. 12, or can utilize an architecture completely different than that shown in FIG. 12.

Based on the foregoing, it should be appreciated that technologies for providing a network service capable of identifying infrequently accessed data from a request stream have been disclosed herein. Moreover, although the subject matter presented herein has been described in language specific to computer structural features, methodological acts, and computer readable media, it is to be understood that the invention defined in the appended claims is not necessarily limited to the specific features, acts, or media described herein. Rather, the specific features, acts, and media are disclosed as example forms of implementing the claims.

The subject matter described above is provided by way of illustration only and should not be construed as limiting. Furthermore, the claimed subject matter is not limited to implementations that solve any or all disadvantages noted in any part of this disclosure. Various modifications and changes can be made to the subject matter described herein without following the example configurations and applications illustrated and described, and without departing from the true spirit and scope of the present invention, which is set forth in the following claims.

What is claimed is:

1. A system comprising:
  a wearable patch that is affixable to a user, the wearable patch including at least an accelerometer and a transmitter to transmit movement signals generated by the accelerometer based at least in part on movement of the user and corresponding movement of the wearable patch;
  a motion classification device to determine, from a predefined set of possible motion description data that describes different types of possible movement of the user, based at least in part on the movement signals representing the movement of the user and the corresponding movement of the wearable patch, and without receiving additional data indicating an activity of the user, motion description data classifying a specific type of movement exhibited by the user, the specific type of movement being determined based at least in part on a repeatable series of movements or previously identified patterns extracted from the movement signals;
  an analytics device to:
    receive the movement signals and the motion description data;
    generate a historical profile for the user of the wearable patch based at least in part on the movement signals and the motion description data;
    create a metric threshold based at least in part on the historical profile to indicate when subsequent movement data indicates at least one of fatigue of the user or a potential injury of the user; and
    analyze the first movement signals and the motion description data associated with the movement signals to determine user information including at least one of a first likelihood of fatigue of the user, a second likelihood of injury of the user, or a predicted type of injury associated with the user; and an output device to receive the user information from the analytics device, the output device to cause display of the user information in response to at least one of the first likelihood of fatigue or the second likelihood of injury reaching or exceeding the metric threshold.

2. The system as recited in claim 1, wherein the motion classification device is further configured to:
   receive imagery of the movement of the user; and
   analyze the imagery to create the motion description data based at least in part on the predefined set of possible motion description data, where in the motion description data indicates a specific athletic movement.

3. The system as recited in claim 1, wherein the first movement signals are created during a time interval characterized by the motion description data representing the movement of the user.

4. The system as recited in claim 1, wherein the analytics device creates different historical profiles for different motion description data.

5. The system as recited in claim 1, wherein the motion description data includes physical therapy motions defining predefined movement profiles of specific limbs of a body.

6. The system as recited in claim 1, wherein the wearable device is associated with a specific location on a specific appendage of the user, and wherein the historical profile is based at least in part on the specific location on the specific appendage.

7. A method comprising:
   receiving, via a data stream, movement data in response to movement of a user;
   receiving motion description data that describes an action associated with the movement data;
   analyzing the movement data based at least in part on historical movement data associated with the motion description data to determine a movement metric;
   comparing the movement metric to a threshold value;
   determining, based at least in part on the movement metric meeting or exceeding the threshold value, at least one of a first likelihood of fatigue of the user or a second likelihood of injury of the user; and
   sending an output to an output device in response to the movement metric meeting or exceeding the threshold value, the output to communicate a status of the user, a recommendation to discontinue performing the action or to perform the action at a reduced level that is less than a previous level at which the user was performing the action, and a minimum period of time to wait to perform the action at the previous level.

8. The method as recited in claim 7, wherein receiving the movement data includes receiving the movement data from a wearable device affixed to the user, and further receiving additional movement data of equipment manipulated by the user while performing an activity described by the motion description data.

9. The method as recited in claim 7, further comprising classifying at least some data of the movement data as practice movement and other data of the movement data as non-practice movement, and further comprising applying a first weight to the practice movement and a second, different weight to the non-practice movement.

10. The method as recited in claim 7, wherein the movement data represents at least one of a physical therapy movement, an exercise movement, a military drill, or a discrete plan of action in a sport.

11. The method as recited in claim 7, wherein the output is at least one of a fatigue prevention indicator or an injury prevention indicator.

12. The method as recited in claim 7, wherein the movement data includes temporal information for a time period that corresponds to the motion description data.

13. The method as recited in claim 7, wherein the analyzing includes using a machine learning model to represent the historical movement data, and further comprising training the machine learning model using feedback received in response to the output.

14. The method as recited in claim 7, wherein the motion data represents accelerometer data of a gait of a stride, and wherein analyzing the movement data based at least in part on a historical movement data associated with the motion description data includes determining differences in at least one of a phase of the movement, a peak range of the movement, or a profile of the movement data.

15. The method as recited in claim 7, further comprising receiving perspiration data in association with the motion data, and wherein the analyzing is based at least in part on the perspiration data.

16. One or more non-transitory computer-readable media storing computer-executable instructions that, when executed on one or more processors, performs acts to:
   receive movement data in response to movement of a human body;
   receive motion description data that describes an action associated with the movement data;
   analyze the movement data based at least in part on historical movement data associated with the motion description data to determine a movement metric, the analyzing including comparing the movement metric to a threshold value;
   determining, based at least in part on the movement metric, that the movement of the human body is non-conforming as compared to an expected type of movement, wherein determining that the movement of the human body is non-conforming is based at least in part on at least one of a rate of movement of the human body, a range of movement of the human body, or an angle of movement of the human body; and
   send an output to an output device based at least in part on the movement metric, the output to communicate a status associated with the human body.

17. The one or more non-transitory computer-readable media as recited in claim 16, wherein the acts further comprise determining, based at least in part on the movement metric, a level or degree of compliance of the movement of the human body with respect to the expected type of movement.

18. The one or more non-transitory computer-readable media as recited in claim 16, wherein the acts further comprise receiving feedback data in response to the output, and wherein the computer-executable instructions that, when executed on one or more processors, further performs acts to train, using the feedback data, a machine learning model that was used to analyze the movement data.

19. The one or more non-transitory computer-readable media as recited in claim 16, wherein the acts further comprise:
   receiving user data in association with the movement data, the user data including at least one of perspiration data, temperature data, or heart rate data;
   receiving ambient data associated with an environment in which the human body is located, the ambient data including at least one of ambient temperature data or ambient humidity data; and determining at least one of the movement metric or the threshold value based at least in part on at least one of the user data or the ambient data.

20. The one or more non-transitory computer-readable media as recited in claim 16, wherein the acts further comprise determining a recommendation based at least in part on the output, the recommendation including at least one of a rest having a specified time, a change in form or position of the human body, or a hydration recommendation.

\* \* \* \* \*